(12) United States Patent
Brucker et al.

(10) Patent No.: US 11,744,993 B2
(45) Date of Patent: Sep. 5, 2023

(54) SYSTEM AND METHOD FOR DEFLECTION MECHANISM WITH EXPANDABLE CONSTRAINT

(71) Applicant: Innovations in Medicine, LLC, Minnetonka, MN (US)

(72) Inventors: Gregory G. Brucker, Minneapolis, MN (US); Steven D. Savage, Lake Havasu City, AZ (US)

(73) Assignee: Innovations in Medicine, LLC, Minnetonka, MN (US)

( * ) Notice: Subject to any disclaimer, the term of this patent is extended or adjusted under 35 U.S.C. 154(b) by 0 days.

(21) Appl. No.: 17/867,528

(22) Filed: Jul. 18, 2022

(65) Prior Publication Data

US 2023/0020076 A1 Jan. 19, 2023

Related U.S. Application Data

(60) Provisional application No. 63/223,383, filed on Jul. 19, 2021.

(51) Int. Cl.
*A61M 25/01* (2006.01)
*A61B 90/00* (2016.01)

(52) U.S. Cl.
CPC ......... *A61M 25/0147* (2013.01); *A61B 90/04* (2016.02); *A61M 25/0136* (2013.01); *A61B 2090/0427* (2016.02); *A61M 25/0138* (2013.01)

(58) Field of Classification Search
CPC .......... A61M 25/0147; A61M 25/0144; A61M 2025/018; A61B 90/04; A61B 90/0427
See application file for complete search history.

(56) References Cited

U.S. PATENT DOCUMENTS

| | | | |
|---|---|---|---|
| 4,734,093 A | 3/1988 | Bonello et al. | |
| 4,930,521 A | 6/1990 | Metzger et al. | |
| 4,983,167 A | 1/1991 | Sahota | |
| 5,045,061 A | 9/1991 | Seifert et al. | |
| 5,170,803 A * | 12/1992 | Hewson | A61N 1/0517 607/124 |
| 5,195,968 A | 3/1993 | Lundquist et al. | |

(Continued)

FOREIGN PATENT DOCUMENTS

| | | |
|---|---|---|
| WO | WO_1991011213 | 8/1991 |
| WO | WO_2015153595 A1 | 10/2015 |
| WO | WO_2016139552 | 9/2016 |

*Primary Examiner* — Carrie R Dorna
(74) *Attorney, Agent, or Firm* — Jonathan M. Rixen; Charles A. Lemaire; Lemaire Patent Law Firm, P.L.L.C.

(57) ABSTRACT

A deflection system for deflecting a body lumen that includes a deflection mechanism, wherein the deflection mechanism includes: a beam having a proximal end and a distal end, wherein the beam includes a neutral position and a deflected position, a pull wire coupled to the distal end of the beam, wherein the beam is configured to be placed in the deflected position when a tension force is applied to the pull wire, and wherein at least a portion of the pull wire is configured to move to a displacement distance away from the beam when the tension force is applied to the pull wire, and one or more constraint members operatively coupled to the beam, wherein each one of the one or more constraint members is configured to limit the displacement distance of the pull wire from the beam when the tension force is applied to the pull wire.

18 Claims, 21 Drawing Sheets

(56) References Cited

U.S. PATENT DOCUMENTS

| | | | |
|---|---|---|---|
| 5,467,763 | A | 11/1995 | McMahon et al. |
| 5,531,776 | A | 7/1996 | Ward et al. |
| 5,558,665 | A | 9/1996 | Kieturakis |
| 5,820,591 | A | 10/1998 | Thompson et al. |
| 6,067,990 | A | 5/2000 | Kieturakis |
| 6,148,222 | A | 11/2000 | Ramsey |
| 6,733,500 | B2 | 5/2004 | Kelley et al. |
| 7,621,908 | B2 | 11/2009 | Miller |
| 8,273,016 | B2 | 9/2012 | O'Sullivan |
| 8,454,588 | B2 | 6/2013 | Rieker et al. |
| 8,506,589 | B2 | 8/2013 | Maloney |
| 8,529,443 | B2 | 9/2013 | Maloney |
| 9,119,927 | B1 | 9/2015 | Ratterree et al. |
| 9,668,720 | B2 | 6/2017 | Kasic |
| 9,744,339 | B2 | 8/2017 | Fojtik |
| 9,833,149 | B2 | 12/2017 | Fojtik et al. |
| 9,931,108 | B2 | 4/2018 | Miller |
| 9,937,329 | B2 | 4/2018 | Niazi |
| 10,265,058 | B2 | 4/2019 | Kasic |
| 10,307,149 | B2 | 6/2019 | Kasic et al. |
| 10,307,520 | B2 | 6/2019 | Oza et al. |
| 10,335,133 | B2 | 7/2019 | Fojtik |
| 10,695,041 | B2 | 6/2020 | Fojtik |
| 11,045,251 | B2 | 6/2021 | Miller |
| 11,298,203 | B2 | 4/2022 | Brucker et al. |
| 11,324,874 | B2 | 5/2022 | Oza et al. |
| 2011/0082188 | A1 | 4/2011 | Chakravarti |
| 2014/0094839 | A1 | 4/2014 | Nimkar et al. |

* cited by examiner

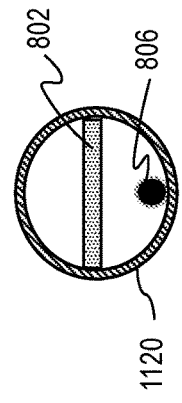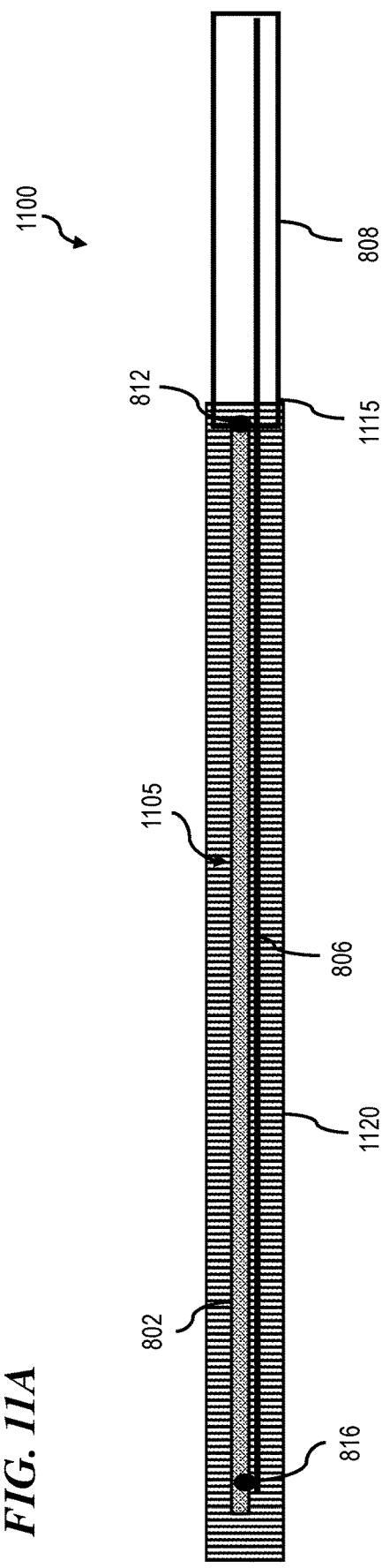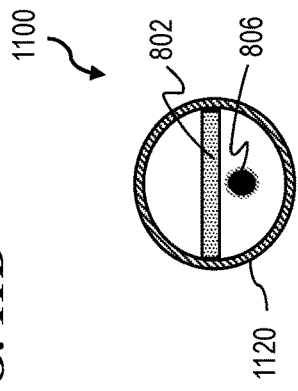

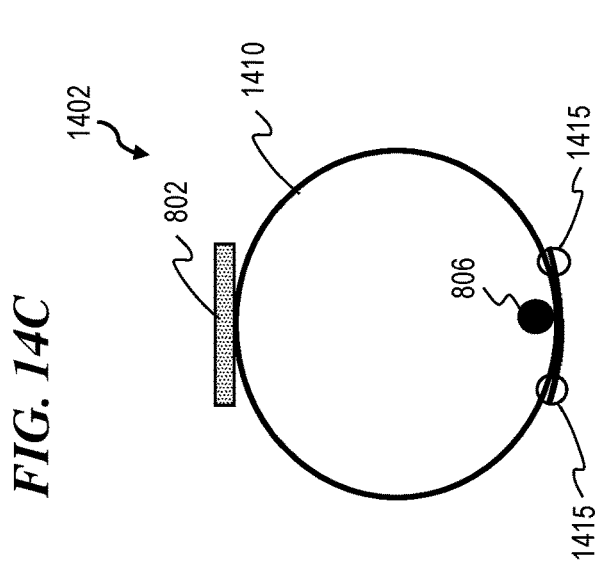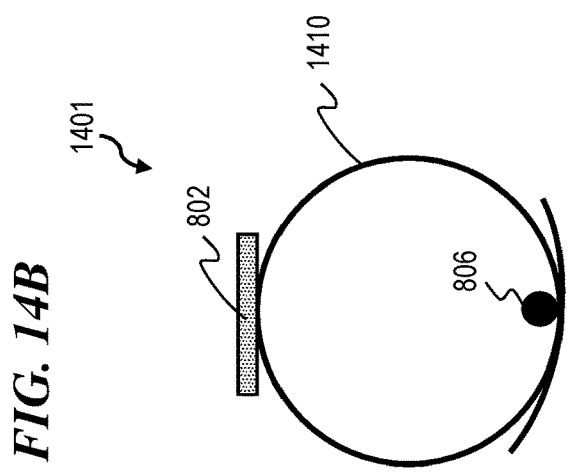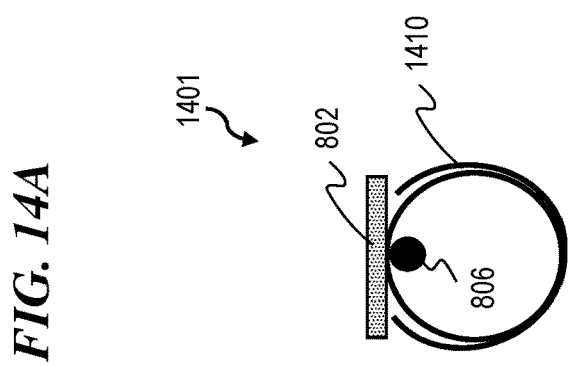

SYSTEM AND METHOD FOR DEFLECTION MECHANISM WITH EXPANDABLE CONSTRAINT

CROSS-REFERENCE TO RELATED APPLICATIONS

This application claims priority benefit, under 35 U.S.C. § 119(e), of U.S. Provisional Patent Application No. 63/223,383, filed Jul. 19, 2021 by Gregory G. Brucker et al., titled "SYSTEM AND METHOD FOR DEFLECTION MECHANISM WITH EXPANDABLE CONSTRAINT," which is incorporated herein by reference in its entirety.

This application is related to prior:
  U.S. Provisional Patent Application 62/426,223, titled "SYSTEM AND METHOD FOR DEFLECTION OF A BODY LUMEN" filed Nov. 23, 2016;
  PCT Patent Application PCT/US2017/063171, titled "SYSTEM AND METHOD FOR DEFLECTION OF A BODY LUMEN" filed Nov. 23, 2017 (published as WO 2018/098388); and
  U.S. Pat. No. 11,298,203, issued Apr. 12, 2022 to Gregory G. Brucker et al. and titled "SYSTEM AND METHOD FOR DEFLECTION OF A BODY LUMEN; each of which is incorporated herein by reference in its entirety.

There are multiple embodiments described herein, each of which can be combined with one or more other embodiments described herein and/or incorporated by reference. In some other embodiments, the present invention provides subcombinations that include most features of the various embodiments, but omit one or more features that are individually shown and described herein.

FIELD OF THE INVENTION

The present invention relates generally to a mechanism for deflection of a body lumen, and in particular to a deflection mechanism and method that provides greater mechanical advantage with which to deflect the body lumen while also limiting the maximum distance the deflection mechanism can move in order to keep the deflection-mechanism movement consistent with the dimensions of the body lumen.

BACKGROUND OF THE INVENTION

In one embodiment of an esophageal, deflection catheter system 101, system 101 is comprised of two independent parts: namely a balloon catheter 105 and a deflection mechanism 160 as shown in FIG. 1. Deflection mechanism 160 includes a beam affixed to a metal tube at its proximal end to anchor the beam and affixed to a pull wire at its distal end to deflect the beam (the beam, metal tube, and pull wire are not shown in FIG. 1 since these components are primarily contained within catheter shaft 121). Balloon catheter 105 includes a catheter shaft 121 comprised of a plastic tube to which is attached one or more balloons 170. In some embodiments, a Tuohy Borst hub 140 is attached to the proximal end of the catheter shaft 121, and, in some embodiments, deflection mechanism 160 includes a handle 165 coupled to hub 140. In some embodiments, catheter shaft 121 includes metal bands 123 interspersed between balloons 170 and also distal to the most distal balloon and proximal to the most proximal balloon 170 such that each balloon 170 is demarcated by a metal ring 123 on either side of the balloon 170 for purposes of visualization, such as by fluoroscopy. In some embodiments, one or more skive hole(s) 124 serves as a port through which fluids are injected into or extracted from the luminal volume between two balloons and the interior surface of a body lumen. In some embodiments, catheter shaft 121 includes one or more ports 125 configured for injection or extraction of fluids. In some embodiments, balloons 170 are in fluid communication with a port within the hub 140 to inflate/deflate the balloons. In some embodiments, the central lumen of catheter shaft 121 contains the beam and pull wire of deflection mechanism 160. The maneuverability of the deflection mechanism 160 allows it to be positioned within the balloon catheter 105 and deflected to achieve the desired spatial position, for example, a deflected esophagus in a thoracic cavity relative to the posterior wall of the heart.

In operation, when esophageal deflection is desired, the balloon catheter 105 is inserted through the throat into the esophagus and positioned at a desired location relative to the heart. The balloon(s) are inflated to expand the esophagus in order to maintain a circular cross-sectional profile during deflection. The deflection mechanism 160 is then positioned both longitudinally and rotationally within the catheter 105 to achieve the desired deflection of the esophagus relative to the posterior wall of the heart. The said esophageal deflection allows cardiac ablation on the posterior wall of the heart to be performed safely and more effectively to treat atrial fibrillation. Movement of the esophagus is achieved by tensioning a pull wire of deflection mechanism 160 which causes the beam to curve into an arc which in turn causes the catheter to deflect away from its centerline. Increasing tension on the pull wire increases the depth of the arc causing a larger deflection from the centerline of the catheter 105. Similarly, deflection of other body lumens relative to critical structures can be obtained using deflection catheter system 101. When positioned inside a body lumen, the body lumen moves in conjunction with deflection catheter system 101.

One issue encountered with this design is the difficulty of deflecting a body lumen which is externally constrained by other structures or body tissue such as by connective tissue surrounding the esophagus. This situation contrasts with that of a steerable catheter, such as those used in electrophysiology for cardiac ablation or in angioplasty for treatment of coronary artery disease, in which the deflection mechanism is used to redirect a catheter tip to achieve a desired location. Many body lumens, including the esophagus, have fibrous connections to surrounding tissue which generate external forces which must be overcome to achieve the desired degree of translation. These additional forces on the deflection catheter alter the distribution of mechanical forces within the deflection mechanism, resulting in a significant increase in pull forces required to deflect the body lumen. This required increased pull force is generally difficult to achieve with current deflectable catheter designs because the pull wire in these designs is tightly constrained by a catheter body structure, reducing the ability of the pull wire to gain mechanical advantage to assist in deflecting a body lumen.

The effect of the lack of mobility of a pull wire imposed by a balloon catheter on a deflection mechanism can be best understood in accordance with FIG. 2A through FIG. 3. FIG. 2A illustrates a design of the distal end of a typical deflection mechanism 200 in its neutral state, i.e., no curvature. Deflection mechanism 200 includes beam 202 of a fixed length defined by the desired length of a deflected body lumen to which support tube 208 is attached on its proximal end by means of joint 212. Support tube 208 extends to the handle of the deflection mechanism 200 (not shown) where it is fixed within a handle (not shown). Pull wire 206 is anchored to the distal end of beam 202 at joint 216. Pull wire 206 runs along beam 202, through center of the support tube 208, through the handle (not shown) and terminates in a sliding mechanism (not shown) which is used to tension pull wire 206 to deflect a beam 202 and hence a body lumen.

FIG. 2B illustrates a deflection mechanism 200 which has been deflected a certain distance from its neutral or straight state. In this configuration, during deflection, pull wire 206 is tensioned using a slide mechanism in a handle (not shown). Because the length of pull wire 206 shortens between points 212 and 216, beam 202 curves to form an arc defined by end points 212 and 216. Because there are no constraints on lateral movement of pull wire 206 away from beam 202, the pull wire forms a chord to the arc defined by points 216 and 212. The resulting curvature of beam 202 is the mechanism by which deflection displaces a body lumen laterally away from its longitudinal axis. This configuration represents the maximum distance a pull wire 206 can be displaced from beam 202 in a curved or deflected configuration.

FIG. 3 illustrates a deflection mechanism 300 in which pull wire expansion (i.e., the distance between pull wire 206 and beam 202) is constrained by an internal lumen of a catheter shaft. In this configuration, the internal wall of catheter lumen 320 acts to limit the lateral movement of pull wire 206 away from beam 202 during deflection. Because of this constraint, pull wire 206 assumes the shape of an arc as shown in FIG. 3 instead of a chord as shown in FIG. 2B. This change in orientation of pull wire 206 relative to beam 202 in FIG. 3 results in higher tensile forces in the pull wire for the same beam curvature when compared to an unconstrained pull wire 206 as shown in FIG. 2B. This difference (i.e., the difference in tensile forces) is rooted in the physics of beam deflection in which forces perpendicular to a beam cause displacement or curvature, the perpendicular force being higher in an unconstrained pull wire configuration.

U.S. Pat. No. 4,930,521 by William T. Metzger et al., titled "VARIABLE STIFFNESS ESOPHAGEAL CATHETER", issued on Jun. 5, 1990 and is incorporated herein by reference.

U.S. Pat. No. 5,467,763 by Michael J. McMahon et al., titled "SURGICAL INSTRUMENTS", issued on Nov. 21, 1995 and is incorporated herein by reference.

U.S. Pat. No. 5,558,665 by Maciej J. Kieturakis, titled "SURGICAL INSTRUMENT AND METHOD FOR INTRALUMINAL RETRACTION OF AN ANATOMIC STRUCTURE", issued on Sep. 24, 1996 and is incorporated herein by reference.

U.S. Pat. No. 6,148,222 by Maynard Ramsey, titled "ESOPHAGEAL CATHETERS AND METHOD OF USE", issued on Nov. 14, 2000 and is incorporated herein by reference.

U.S. Pat. No. 7,621,908 by Steven W. Miller, titled "CATHETER FOR MANIPULATION OF THE ESOPHAGUS", issued on Nov. 24, 2009 and is incorporated herein by reference.

U.S. Pat. No. 8,273,016 by Martin F. O'Sullivan, titled "ESOPHAGUS ISOLATION DEVICE", issued on Sep. 25, 2012 and is incorporated herein by reference.

U.S. Pat. No. 8,454,588 by Gregory B. Rieker et al., titled "METHOD AND APPARATUS TO PREVENT ESOPHAGEAL DAMAGE", issued on Jun. 4, 2013 and is incorporated herein by reference.

U.S. Pat. No. 8,506,589 by James D. Maloney, titled "NASOGASTRIC TUBE FOR USE DURING AN ABLATION PROCEDURE", issued on Aug. 13, 2013 and is incorporated herein by reference.

U.S. Pat. No. 8,529,443 by James D. Maloney, titled "NASOGASTRIC TUBE FOR USE DURING AN ABLATION PROCEDURE", issued on Sep. 10, 2013 and is incorporated herein by reference.

U.S. Pat. No. 9,668,720 by James F. Kasic, titled "SYSTEMS, DEVICES, COMPONENTS AND METHODS FOR DISPLACING AND REPOSITIONING THE ESOPHAGUS AWAY FROM THE HEART DURING ATRIAL ABLATION SURGICAL PROCEDURES", issued on Jun. 6, 2017 and is incorporated herein by reference.

U.S. Pat. No. 9,744,339 by Shawn P. Fojtik, titled "APPARATUS FOR MANUALLY MANIPULATING HOLLOW ORGANS", issued on Aug. 29, 2017 and is incorporated herein by reference.

U.S. Pat. No. 9,833,149 by Shawn P. Fojtik et al., titled "METHODS, APPARATUS AND SYSTEMS FOR FACILITATING INTRODUCTION OF SHAPED MEDICAL INSTRUMENTS INTO THE BODY OF A SUBJECT", issued on Dec. 5, 2017 and is incorporated herein by reference.

U.S. Pat. No. 9,931,108 by Steven Miller, titled "SYSTEM AND METHOD FOR INFLUENCING AN ANATOMICAL STRUCTURE", issued on Apr. 3, 2018 and is incorporated herein by reference.

U.S. Pat. No. 9,937,329 by Imran K. Niazi, titled "INTRA-ESOPHAGEAL BALLOON SYSTEM", issued on Apr. 4, 2018 and is incorporated herein by reference.

U.S. Pat. No. 10,265,058 by James F. Kasic, titled "SYSTEMS, DEVICES, COMPONENTS AND METHODS FOR DISPLACING AND REPOSITIONING THE ESOPHAGUS AWAY FROM THE HEART DURING ATRIAL ABLATION SURGICAL PROCEDURES", issued on Apr. 23, 2019 and is incorporated herein by reference.

U.S. Pat. No. 10,307,149 by James F. Kasic et al., titled "INTRALUMINAL RETRACTOR", issued on Jun. 4, 2019 and is incorporated herein by reference.

U.S. Pat. No. 10,307,520 by Veeral M. Oza et al., titled "SYSTEMS AND METHODS FOR MECHANICAL DISPLACEMENT OF AN ESOPHAGUS", issued on Jun. 4, 2019 and is incorporated herein by reference.

U.S. Pat. No. 10,335,133 by Shawn P. Fojtik, titled "EXPANDABLE DEVICES FOR POSITIONING ORGANS", issued on Jul. 2, 2019 and is incorporated herein by reference.

U.S. Pat. No. 10,695,041 by Shawn P. Fojtik, titled "EXPANDABLE DEVICES FOR POSITIONING ORGANS", issued on Jun. 30, 2020 and is incorporated herein by reference.

U.S. Patent Application Publication 2014/0094839 by Shekhar Nimkar et al., titled "MECHANICAL TENSIONING DEVICE", published on Apr. 3, 2014 and is incorporated herein by reference.

SUMMARY OF THE INVENTION

In one embodiment of the present invention, a deflection mechanism with expandable constraints for manipulating a body lumen is comprised of a beam, a pull wire and one or more expandable constraints. In some embodiments, the expandable constraints are designed to allow a pull wire to move away from the beam during deflection to provide greater mechanical advantage with which to deflect the beam but limit the maximum distance the pull wire can move to a value less than that achievable in the absence of constraints. The advantage of this design is a reduction in force a pull wire must exert on a beam to deflect a body lumen, especially one constrained within a body cavity along its length, for example by connective tissue. Another advantage of a dynamically expandable constraint is maintenance of a smaller device diameter in its non-deflected state, allowing for easier introduction into a body cavity.

In another embodiment of the present invention for use in a clinical setting, the deflection mechanism is covered with a thin-walled flexible tube to prevent fluid infiltration and damage to the deflection mechanism or surrounding tissue during clinical use.

In some embodiments of a deflection mechanism with expandable constraints according to the present invention, a deflection mechanism with expandable constraints is combined with a catheter containing an expandable element for the purpose of deflecting a body lumen. In some embodiments of this concept, the invention includes a catheter shaft having a first lumen within the catheter shaft extending through at least a length of the catheter shaft, at least one inflatable and deflatable balloon located along the catheter shaft and operably coupled to said first lumen and configured to expand in diameter within a target lumen to form an expanded first portion of the apparatus, and a lateral deflection mechanism operably coupled within a catheter shaft, wherein the lateral deflection mechanism includes a beam, a pull wire, and expandable constraint(s) operably coupled to the beam and pull wire, wherein the expandable constraints permit movement of the pull wire away from the beam while also limiting the distance the pull wire can travel to a value less than the maximum possible distance in the absence of constraints.

In some embodiments of a deflection mechanism with expandable constraints according to the present invention for deflection of a body lumen, the combination of a deflection mechanism and balloon catheter are designed to combine a mechanical approach with an expandable-element approach to obtain the benefits of more reliable positioning, larger body lumen deflection and easier clinical use. These benefits are derived from features which collectively provide the following desirable clinical advantages: First is an expansion catheter that includes a catheter shaft with one or more expansion elements along its outer surface. The expansion element(s) serve to enlarge a body lumen to reduce its elasticity and deformability when manipulated, effectively fixing the relationship between the expansion catheter and the body lumen. Second is a deflection mechanism which resides within a catheter shaft which, when manipulated, causes the catheter shaft to deviate from its neutral state to a curved state in which a least a portion of the catheter shaft is displaced laterally while simultaneously displacing a body lumen in contact with the expansion element(s). Third is an expansion element and deflection mechanism which are movable with respect to each other in order to locate and more easily deflect a portion of a catheter relative to a body structure. Fourth is a deflection mechanism which contains expandable constraints on lateral movement of a pull wire which allow the pull wire to move away from the beam to achieve a larger mechanical advantage to more effectively utilize the tensile force of a pull wire to deflect the beam within the confines of a body luminal diameter. Fifth is a smaller device diameter in its non-deflected state for ease of introduction into a body lumen.

BRIEF DESCRIPTION OF THE DRAWINGS

FIG. 11A is a schematic diagram of a deflection assembly 1100, according to one embodiment of the present invention.

FIG. 11B is a cross-sectional view of deflection assembly 1100 as viewed toward the right-hand side of FIG. 11A from the middle of deflection assembly 1100, with beam 802 in its neutral or undeflected state, according to one embodiment of the present invention.

FIG. 11C is a cross-sectional view of deflection assembly 1100 as viewed toward the right-hand side of FIG. 11A from the middle of deflection assembly 1100, with beam 802 in its deflected state and pull wire 806 moved laterally away from beam 802, according to one embodiment of the present invention.

FIG. 14A is a cross-sectional view of a deflection assembly 1401 with beam 802 in its neutral or undeflected state, according to one embodiment of the present invention.

FIG. 14B is a cross-sectional view of deflection assembly 1401 with beam 802 in its deflected state and pull wire 806 moved laterally away from beam 802, according to one embodiment of the present invention.

FIG. 14C is a cross-sectional view of a deflection assembly 1402 with beam 802 in its deflected state and pull wire 806 moved laterally away from beam 802, according to one embodiment of the present invention.

DETAILED DESCRIPTION

Figure 1:
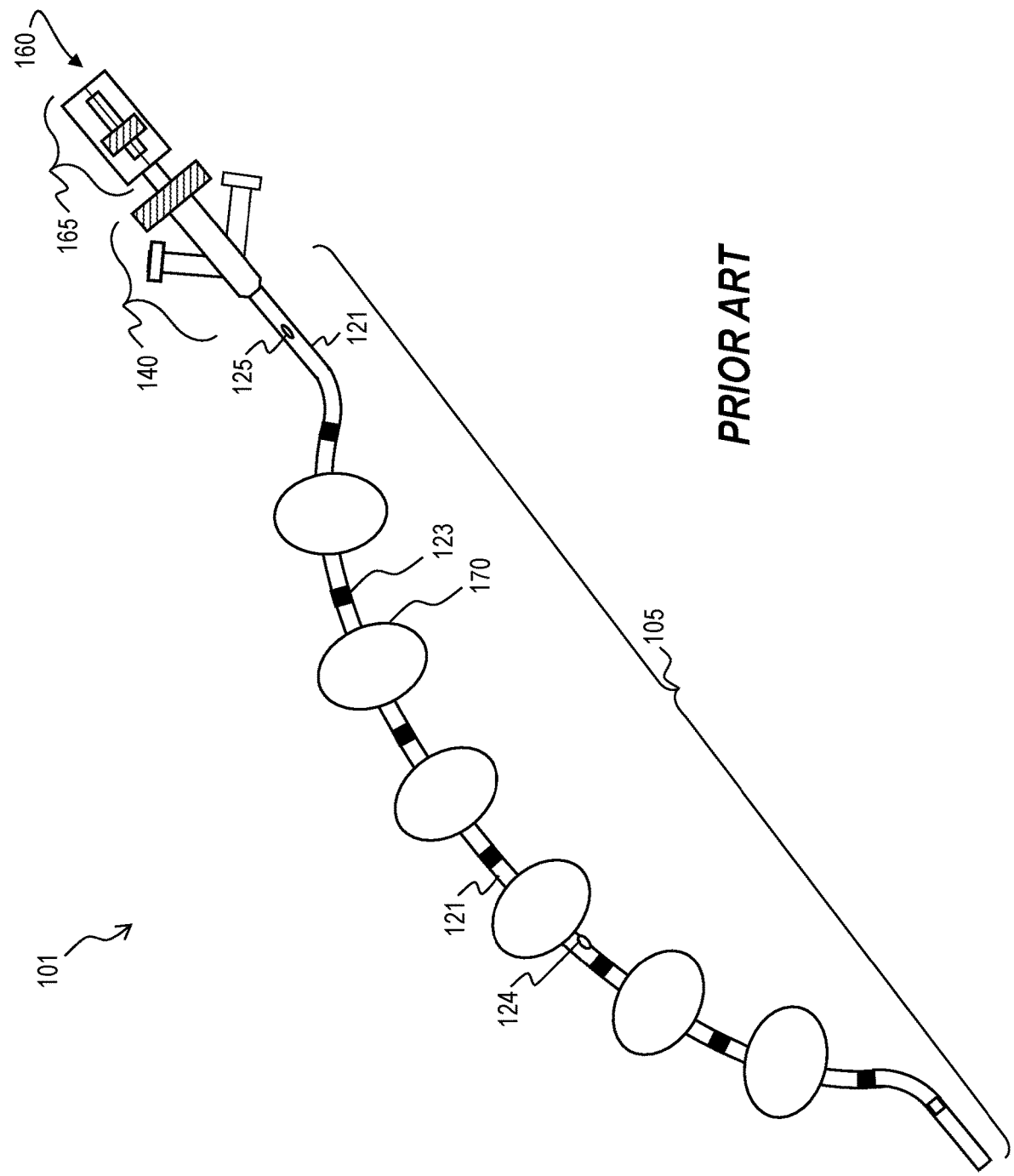
FIG. 1 is a schematic diagram of a deflection catheter system 101.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following embodiments of the invention are set forth without any loss of generality to, and without imposing limitations upon the claimed invention. Further, in the following detailed description of the embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The embodiments shown in the Figures and described here may include features that are not included in all specific embodiments. A particular embodiment may include only a subset of all of the features described, or a particular embodiment may include all of the features described.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter to material associated with such marks.

In most conventional deflectable catheters, a thin wire is used to apply a force to a catheter shaft to deflect a distal portion from its longitudinal axis, causing a change in shape for the purpose of redirecting a catheter within a body cavity. A pull wire is typically housed within a small lumen in a catheter shaft causing the pull wire to be highly constrained by the luminal walls of the catheter and thus remain parallel to the longitudinal axis of the catheter. This constrained alignment of the pull wire causes most of its force to be directed along the catheter longitudinal axis, with only a small force directed perpendicular to the axis for the purpose of changing the shape of its distal region. For most applications this applied force is adequate to manipulate the tip of a catheter, for example to steer a tip for the purpose of redirecting a catheter over a small distance. However, for some applications, this force is inadequate to achieve larger deflections of a body lumen over longer distances, for example, esophageal deflection requiring 6 cm deflection over a distance of 16 cm. This situation is compounded by forces created by connective tissues which are present to stabilize a body lumen, forces which also must be overcome to deflect a body lumen. One way to overcome this limitation is to provide a larger mechanical advantage for a pull wire, for example by allowing the pull wire to operate in larger space, thereby increasing the percentage of the pull wire force directed laterally rather than longitudinally. For most catheter designs, which are made of harder-durometer materials with little elasticity and small overall diameters, this is very difficult to achieve. One goal of the present invention is to provide a deflection mechanism with an expandable constraint which allows a pull wire to occupy a much larger space during deflection to provide more lateral movement of a pull wire to gain mechanical advantage, but still limit a pull wire to movement consistent with the dimensions of a body lumen.

Figure 4A:
FIG. 4A is a schematic diagram 401 showing the forces associated with a deflection beam having an attached pull wire, according to one embodiment of the present invention.
Figure 4B:
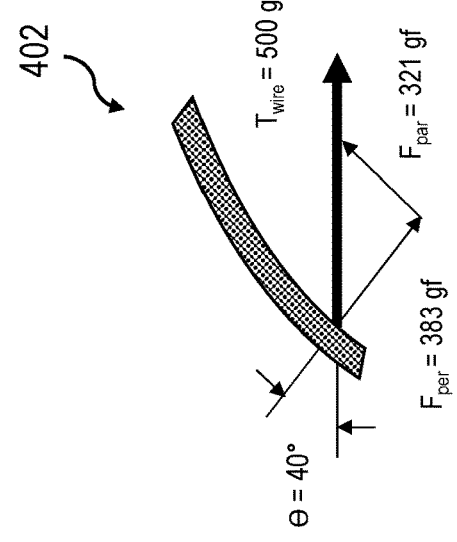
FIG. 4B is a schematic diagram 402 showing the forces associated with the unconstrained configuration of deflection mechanism 200 of FIG. 2B, according to one embodiment of the present invention.
Figure 4C:
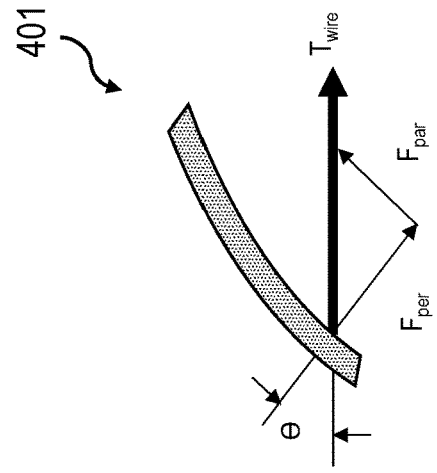
FIG. 4C is a schematic diagram 403 showing the forces associated with the constrained configuration of deflection mechanism 300 of FIG. 3, according to one embodiment of the present invention.

The effect of a constraint on deflection forces in a beam is more easily understood with reference to FIGS. 4A-4C. FIG. 4A shows a force diagram 401 illustrating a distal end of a beam with an attached pull wire, according to one embodiment of the present invention. The tensile force, $T_{wire}$, of FIG. 4A can be resolved into a force perpendicular to the beam, $F_{per}$, which is the force that deflects the beam and a force parallel to the beam, $F_{par}$ which creates tension in the pull wire. These two orthogonal forces are related to the tensile force in the wire, $T_{wire}$, by an angle $\ominus$, the angle that the pull wire makes with the beam as shown in FIG. 4A. Using trigonometry, the tensile force in the wire can be resolved into its orthogonal components as follows:

$F_{per} = T_{wire} \times \cos(\ominus)$ $F_{par} = T_{wire} \times \sin(\ominus)$ Using these equations, the effect of a constraint on deflection forces can be illustrated in the context of an esophageal application in which a 2.5-cm-diameter esophagus is deflected 6 cm over a longitudinal distance of 16 cm by applying a 500 grams-force tensile force to pull wire 206 (as used herein, one (1) "gram-force" is equal to a mass of one gram multiplied by the standard acceleration due to gravity on Earth, which is 9.80665 meters per second squared (m/s²), and one (1) gram-force (gf) is equivalent to 0.00980665 newtons; accordingly, for example, 500 grams-force of tensile force is equivalent to 4.903325 newtons of tensile force).

Figure 2A:
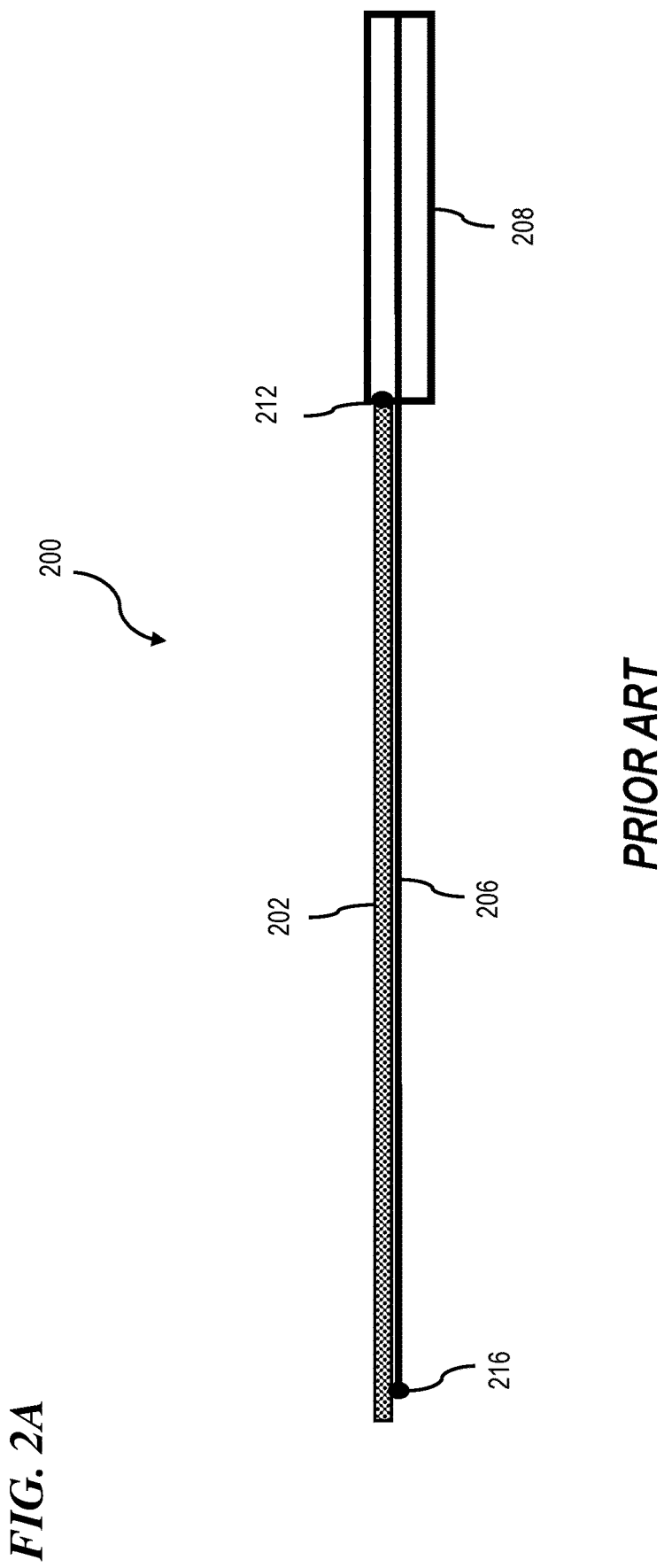
FIG. 2A is a schematic diagram of the distal end of a typical deflection mechanism 200 in its neutral state.
Figure 2B:
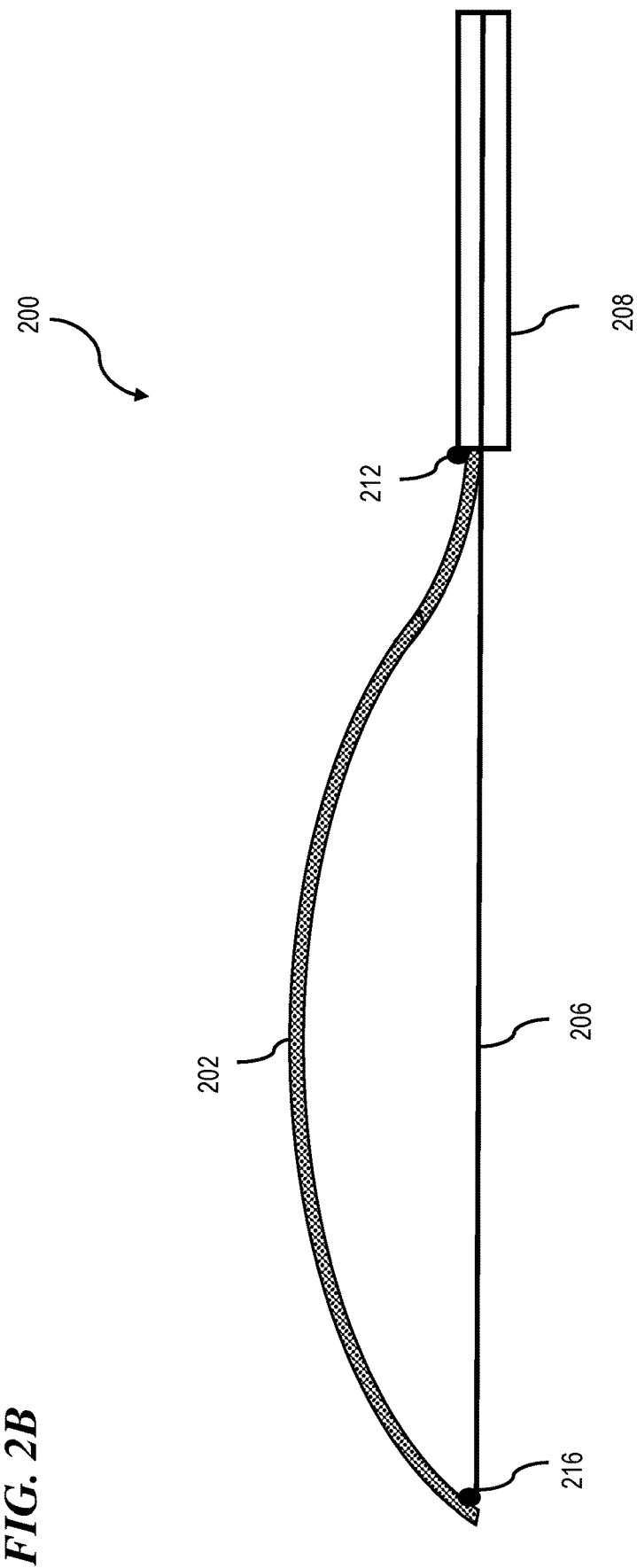
FIG. 2B is a schematic diagram of deflection mechanism 200 that has been deflected a certain distance from its neutral or straight state.

FIG. 4B shows a force diagram 402 for the unconstrained configuration of FIG. 2B, according to one embodiment of the present invention. For this configuration, the angle $\ominus$ is approximately 40 degrees, which yields a calculated perpendicular force $F_{per}=383$ grams-force. FIG. 4C shows a force diagram 403 for the constrained configuration of FIG. 3 in which a deflection mechanism is contained within a catheter internal lumen having a diameter of 6 mm. For this configuration, the angle $\ominus$ is approximately 86 degrees, which yields a perpendicular force $F_{per}=35$ grams-force. Comparing forces, the constrained configuration results in an approximate 10-fold reduction in the perpendicular force for deflecting a beam.

Returning to the clinical application of esophageal deflection, in some embodiments a beam is 0.5 mm thick, 7 mm wide and 16 cm long. Using an equation for a simply supported beam with one end constrained, the force required to deflect the cited beam 6 cm is approximately 40 grams-force.

Figure 3:
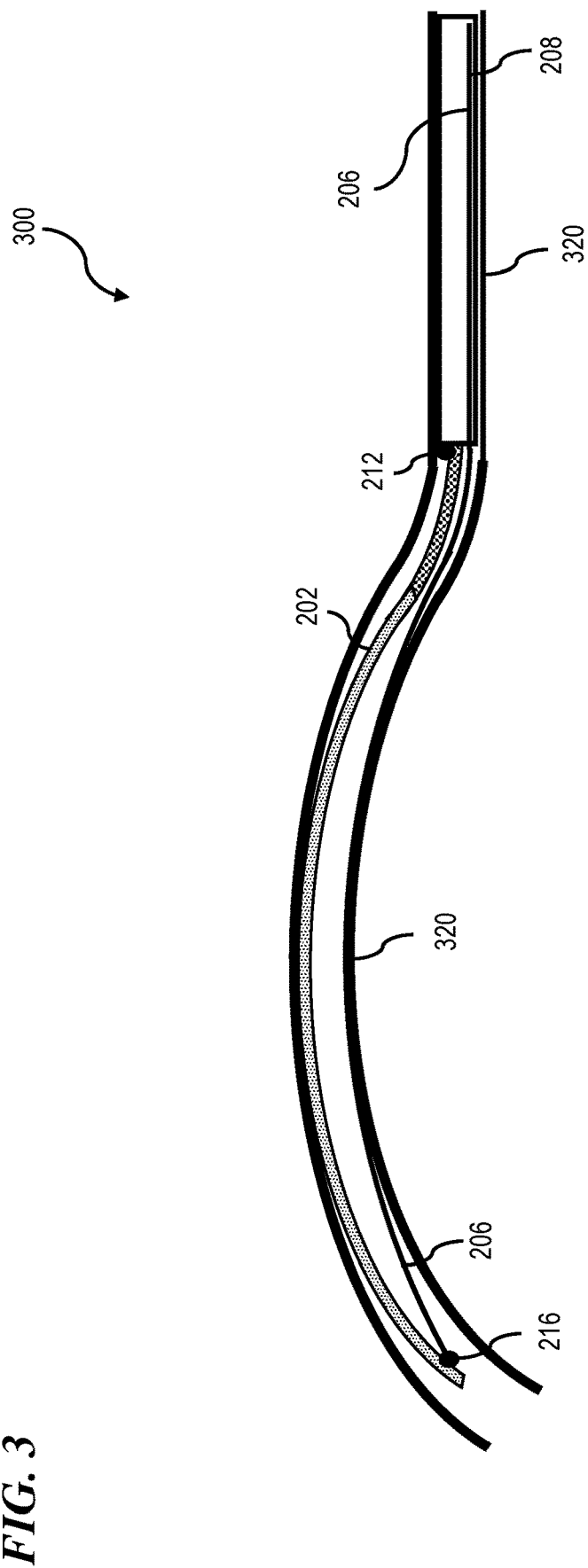
FIG. 3 is a schematic diagram of a deflection mechanism 300 in which pull wire expansion is constrained by an internal lumen of a catheter shaft.

FIG. 4C is a schematic diagram 403 showing the forces associated with the constrained configuration of deflection mechanism 300 of FIG. 3, according to one embodiment of the present invention. As shown in FIG. 4C, even in a constrained configuration, a tension of 500 grams-force in the pull-wire provides sufficient force to deflect the beam, a force which is reasonable to achieve in a typical deflection catheter. However, if 430 grams-force is applied perpendicular to the beam to simulate lateral forces imposed by esophageal body constraints, the beam must now overcome this additional 430 grams-force plus the deflection force of 40 grams-force in order to deflect the esophagus. For the unconstrained configuration of FIG. 4B, using an angle of 40 degrees, requires a tensile force of 613 grams-force to obtain a deflection force of 470 grams-force. For the constrained configuration of FIG. 4C, using an 86-degree angle, the pull wire tensile force becomes 6,737 grams-force to obtain a deflection force of 470 grams-force. This higher force for the constrained configuration is obtainable with mechanical advantage in the handle which would require significantly stronger materials of construction. While not prohibitive, this situation is less than desirable in a clinical setting, especially when alternatives are available which are less expensive and safer.

Figure 5:
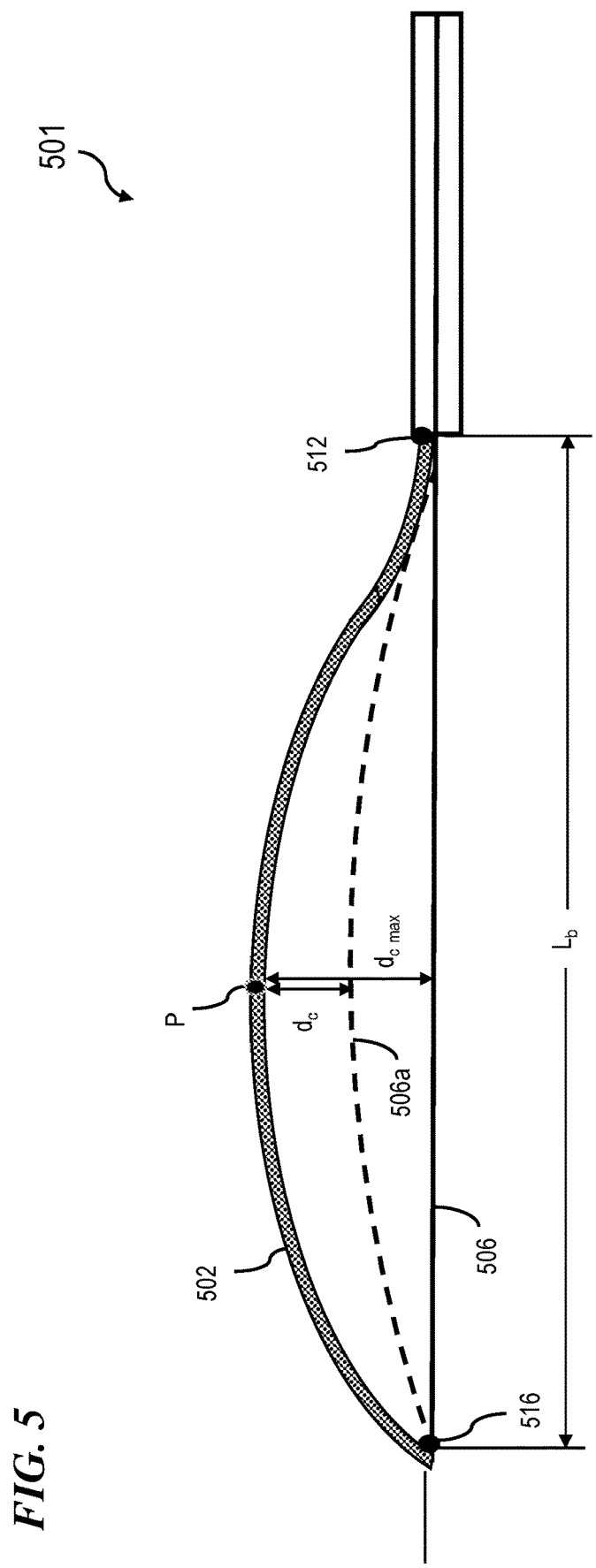
FIG. 5 is a schematic diagram of a deflection mechanism 501, according to one embodiment of the present invention.

To better understand the effect of an expandable constraint on a pull wire in deflection of a body lumen, it is desirable to define terminology specific to this application. FIG. 5 is a schematic diagram of a deflection mechanism 501, according to one embodiment of the present invention. Referring to FIG. 5, a parameter P is defined as the location on the beam of the largest displacement of pull wire 506 between endpoints 516 and 512 from beam 502. Another parameter, $d_c$, is defined as the perpendicular distance between the curved beam at point P and the pull wire shown as dotted line 506a in FIG. 5, which represents the position of a pull wire resulting from the use of constraints (not shown). In addition, parameters $d_{c\ max}$ and $P_{max}$ are defined as the values of $d_c$ and P respectively for an unconstrained pull wire, which is equivalent to a chord connecting points 512 and 516. Another parameter $L_b$ is defined as the linear distance of the beam between two end points 516 and 512 when the beam is in its neutral or non-deflected state.

Using these definitions, an expansion ratio, ER, is defined as the actual distance $d_c$ in a constrained configuration to the maximum possible distance in a configuration without a constraint $d_{c\ max}$, which can be written as $ER = d_c/d_{c\ max}$ In some embodiments of an esophageal application, the maximum unconstrained deflection is 6 cm. By definition this configuration has an ER=1.0 because $d_c=d_{c\ max}$. If the deflection mechanism is placed inside a catheter with an internal lumen diameter of 5 mm, this configuration would have an ER value of 0.5/6 or 0.0833 assuming the pull wire movement is limited by the diameter of the internal lumen.

Another parameter referred to herein as depth ratio, DR, is defined as the maximum possible deflection obtainable by a deflection device divided by the chord length of the beam in its neutral state, which can be written as $DR = d_{c\ max}/L_b$ In some embodiments of an esophageal application where a deflection of 6 cm is desired over a 15 cm length, DR=6/15=0.4.

Using this terminology, the advantages of a pull wire having the freedom to move laterally away from the beam during deflection is understood in the context of different deflection configurations shown in FIGS. 6A-6D.

Figure 6A:
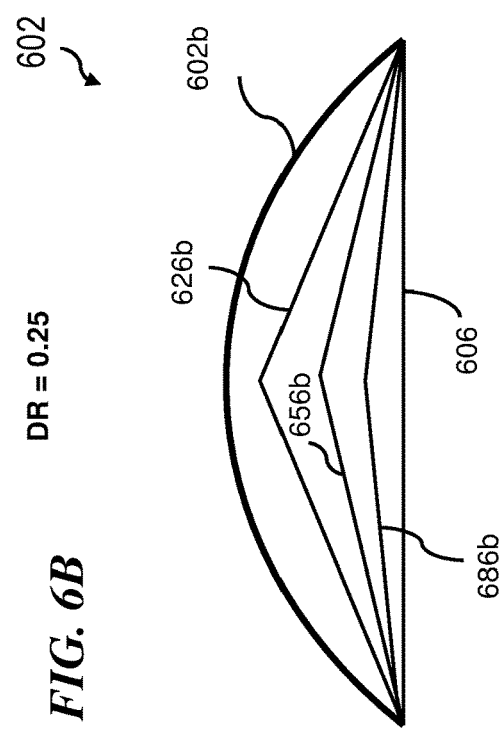
FIG. 6A is a schematic diagram showing a deflection configuration 601 having a depth ratio of 0.5, according to one embodiment of the present invention.

FIG. 6A shows a deflection configuration 601 in which the depth of the curve $d_{c\ max}$ of beam 602a is half the beam length, giving a DR ratio of 0.5, according to one embodiment of the present invention. The pull wire in the unconstrained configuration, ER=1.0, is labelled 606, the pull wire for ER=0.80 is labelled 686*ab*, for ER=0.50 is labelled 656*a*, and for ER=0.20 is labelled 626*a*.

Figure 6B:
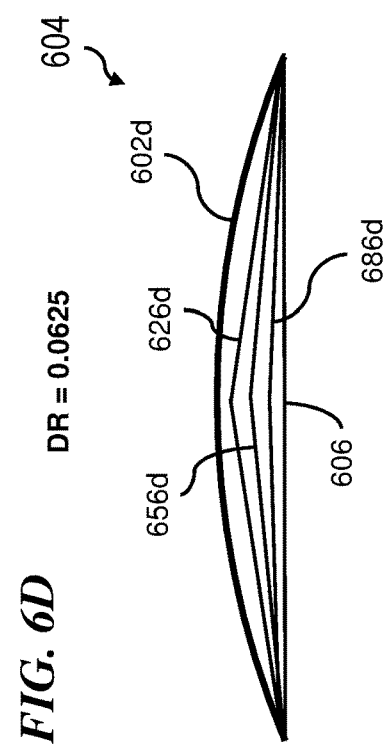
FIG. 6B is a schematic diagram showing a deflection configuration 602 having a depth ratio of 0.25, according to one embodiment of the present invention.

FIG. 6B shows a deflection configuration 602 in which the depth of the curve $d_{c\ max}$ of beam 602*b* is one-fourth the length of the beam, giving a DR ratio of 0.25, according to one embodiment of the present invention. The pull wire in the unconstrained configuration is labelled 606, the pull wire for ER=0.80 is labelled 686*b*, for ER=0.50 is labelled 656*b*, and for ER=0.20 is labelled 626*b*.

Figure 6C:
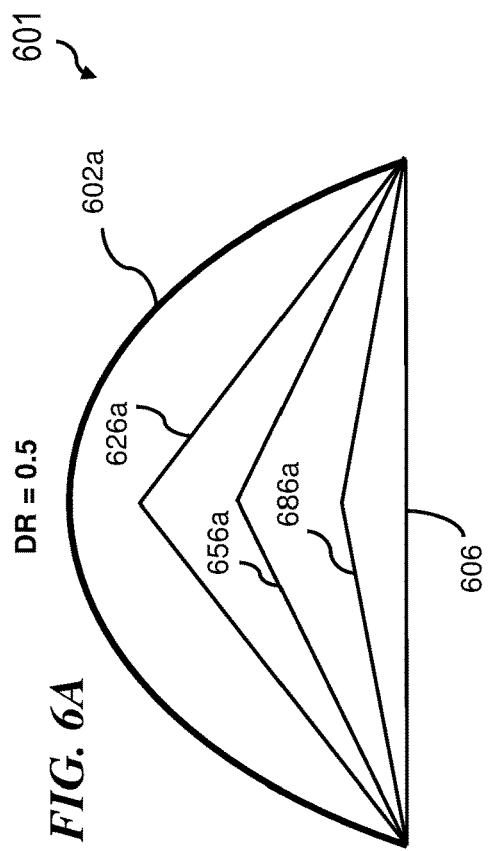
FIG. 6C is a schematic diagram showing a deflection configuration 603 having a depth ratio of 0.125, according to one embodiment of the present invention.

FIG. 6C shows a deflection configuration 603 in which the depth of the curve $d_{c\ max}$ of beam 602*c* is one-eight the length of the beam, giving a DR ratio of 0.125, according to one embodiment of the present invention. The pull wire in the unconstrained configuration is labelled 606, the pull wire for ER=0.80 is labelled 686*c*, for ER=0.50 is labelled 656*c*, and for ER=0.20 is labelled 626*c*.

Figure 6D:
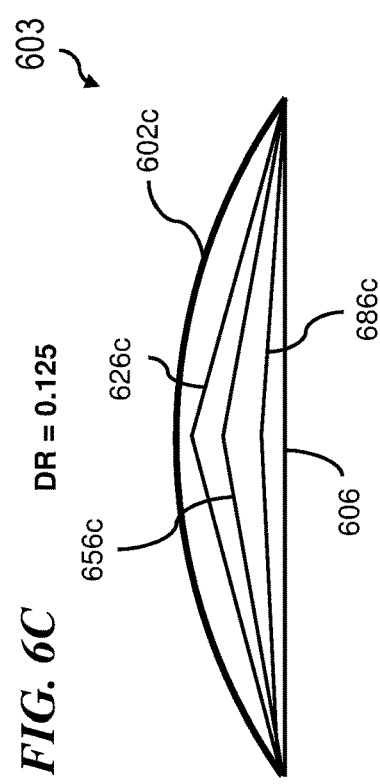
FIG. 6D is a schematic diagram showing a deflection configuration 604 having a depth ratio of 0.0625, according to one embodiment of the present invention.

FIG. 6D shows a deflection configuration 604 in which the depth of the curve $d_c$ max of beam 602*d* is one-sixteenth the length of the chord length, giving an DR ratio of 0.0625, according to one embodiment of the present invention. The pull wire in the unconstrained configuration is labelled 606, the pull wire for ER=0.80 is labelled 686*d*, for ER=0.50 is labelled 656*d*, and for an ER=0.20 is labelled 626*d*.

Figure 7:
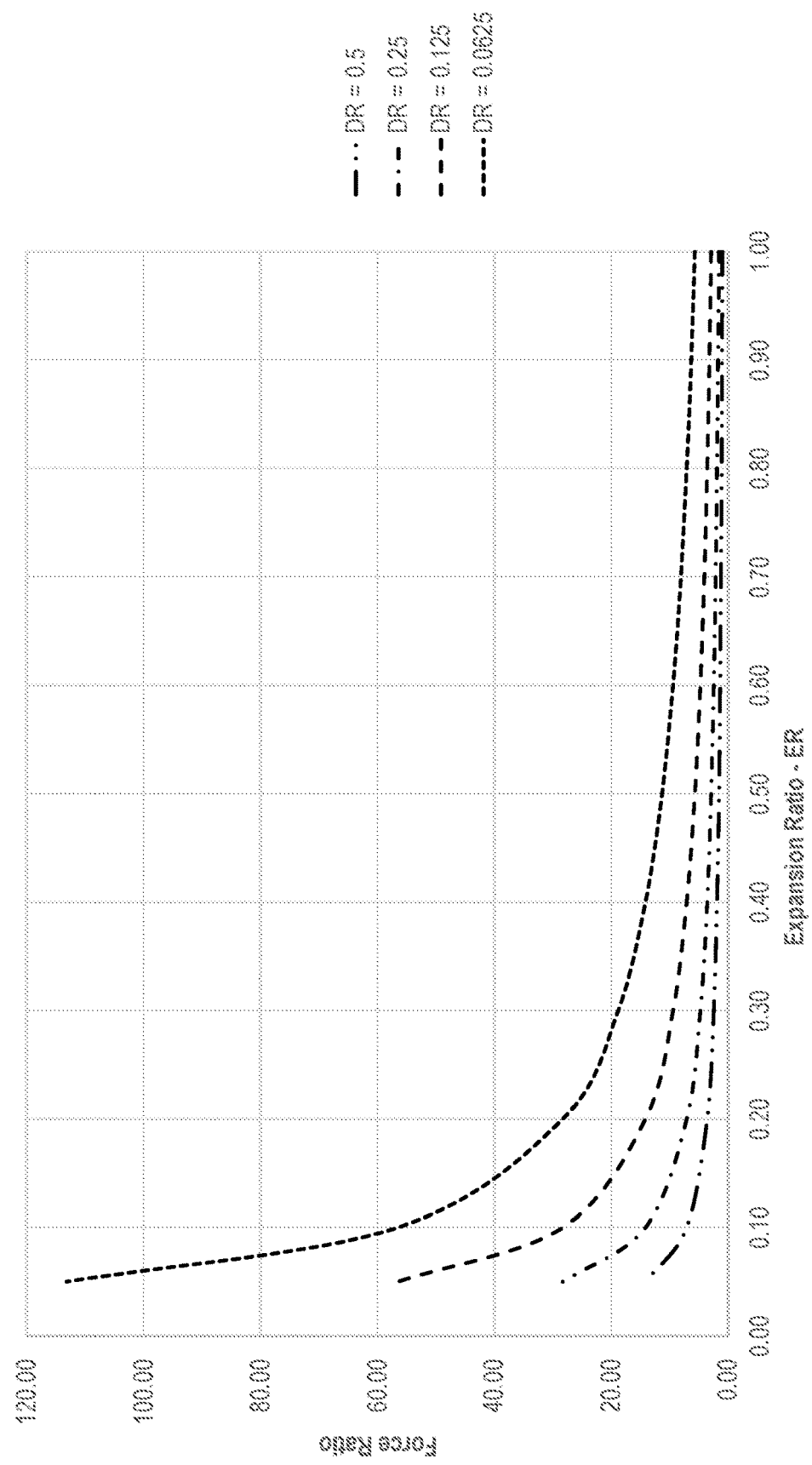
FIG. 7 is a graph 701 showing the effect on pull wire tensile force to deflect an esophagus over a length of 12 cm for various deflection distances, DR, and variable degrees of constraint, ER, the range of which is illustrated in FIG.'s 6A-6D, according to one embodiment of the present invention.

FIG. 7 is a graph 701 showing the effect on pull wire tensile force to deflect an esophagus over a length of 12 cm for various deflection distances, DR, and variable degrees of constraint, ER, the range of which is illustrated in FIGS. 6A-6D, according to one embodiment of the present invention. The horizontal axis represents the expansion ratio, ER. The vertical axis represents the Force Ratio, which is the perpendicular force a pull wire exerts on the beam normalized by the perpendicular force for the configuration DR=0.5 and an ER=1.0. In some embodiments, selection of this configuration for normalization has no other significance than making the data more understandable.

As can be seen in FIG. 7, the effect of an expandable constraint on a pull wire becomes more pronounced as the expansion ratio, ER, becomes smaller, i.e., the pull wire remains closer to the beam during deflection. In the configuration of FIG. 6A where the depth ratio has the largest value, the change in the normalized force between ER=1.0 and 0.1 is approximately 7 to 1, with the lowest ER value having the highest force. This configuration most closely represents that of an esophageal catheter. As the design depth of curvature becomes smaller, the effect of a constraint increases significantly. For a DR=0.0625, the increase in force from ER=1 to ER=0.1 is 56 to 1 compared to 7 to 1 for the previous example. This graph clearly illustrates that allowing a pull wire to move laterally away from the beam, i.e., higher ER values, also reduces the force needed to deflect the beam. This is particularly important in the presence of external constraints that resist lateral deflection and adds to the force the deflection mechanism must overcome to displace a body lumen.

While the unconstrained configuration for a deflection mechanism provides the lowest pull-wire force for deflection and is highly desirable to deflect a body lumen with external constraints, this is not always possible in clinical applications. Generally, there is insufficient internal space within a body lumen or catheter internal lumen to allow for such expansion of a pull wire away from the beam, especially when the deflection mechanism is longer or the required deflection larger. Using an esophageal-deflection application, a pull wire can only move at most 1 inch from the beam before it engages the wall of the esophagus. Having a pull wire engage the inner wall of a body lumen with any significant force is highly undesirable for many reasons. First, once the pull wire engages the vessel wall, the circularity of the vessel is distorted, becoming more elliptical and potentially undoing some benefits of deflection. Second, if unprotected, a pull wire could act as a knife cutting into the vessel wall causing tissue damage and/or possibly rupturing the vessel wall causing collateral damage to surrounding organs. To protect a vessel lumen from such damage but take advantage of the mechanical benefits of a pull wire moving away from the beam, it is desirable, in some embodiments, to have an expandable constraint around the deflection mechanism which limits the said displacement of a pull wire. The expandable constraint acts to allow a pull wire to move away from the beam until a limit is reached beyond which further lateral movement is restricted or impossible. Effectively the expandable constraint acts like a girdle limiting a pull wire to an ER value less than 1 but greater than that which occurs in steering catheter designs which typically have ER values in the range 0.1 or smaller.

Returning to an esophageal application, in some embodiments, it is desirable to limit the movement of a pull wire away from the beam to a maximum distance of 2.5 cm which is the diameter of an expanded esophagus. Since the maximum distance of a pull wire from the beam in some embodiments is 6.0 cm in an unconstrained configuration, the ER value, in some embodiments, is equal to or less than 0.42. This can be obtained by using a constraint which allows a pull wire to touch the wall of the esophagus. Comparatively, a deflection mechanism in which a lumen within the balloon catheter body acts as a constraint on pull wire movement, the ER value is approximately 0.08. In this example, the use of an expandable constraint which allows the pull wire to move away from the beam until it touches the esophageal wall gives an approximately five-fold reduction in pull wire force applied to deflect an esophagus, as illustrated in FIG. 7.

In summary, one goal of the present invention is to provide a deflection mechanism whereby a pull wire can expand laterally away from the beam during deflection. Another goal of the present invention is to provide a means to attain a certain distance between a pull wire and the beam which is greater than the diameter of the crossing profile of the catheter. Another goal of the present invention is to limit the lateral movement of a pull wire to a distance less than that attained by connecting the proximal and distal anchor points of a pull wire to form a chord of an arc created by the deflection. Another goal of the present invention is to provide a constraint around the deflection assembly which is expandable from a smaller diameter to a larger diameter. Another goal of the present invention is to provide a constraint which allows lateral movement of a pull wire to a certain expanded distance, after which increased lateral movement is significantly reduced or eliminated. Another goal of the present invention is to operably couple a catheter shaft containing one or more expandable elements with a deflection mechanism with expandable constraints. Another goal of the present invention is to reduce forces in a pull wire of the deflection assembly to more easily and safely deflect a body lumen in a clinical application. Another goal of the present invention is to provide a means whereby a deflected vessel is visible under fluoroscopy to determine the position of a body lumen with respect to critical structures, for example, an esophagus relative to the posterior wall of the left atrium.

Figure 8A:
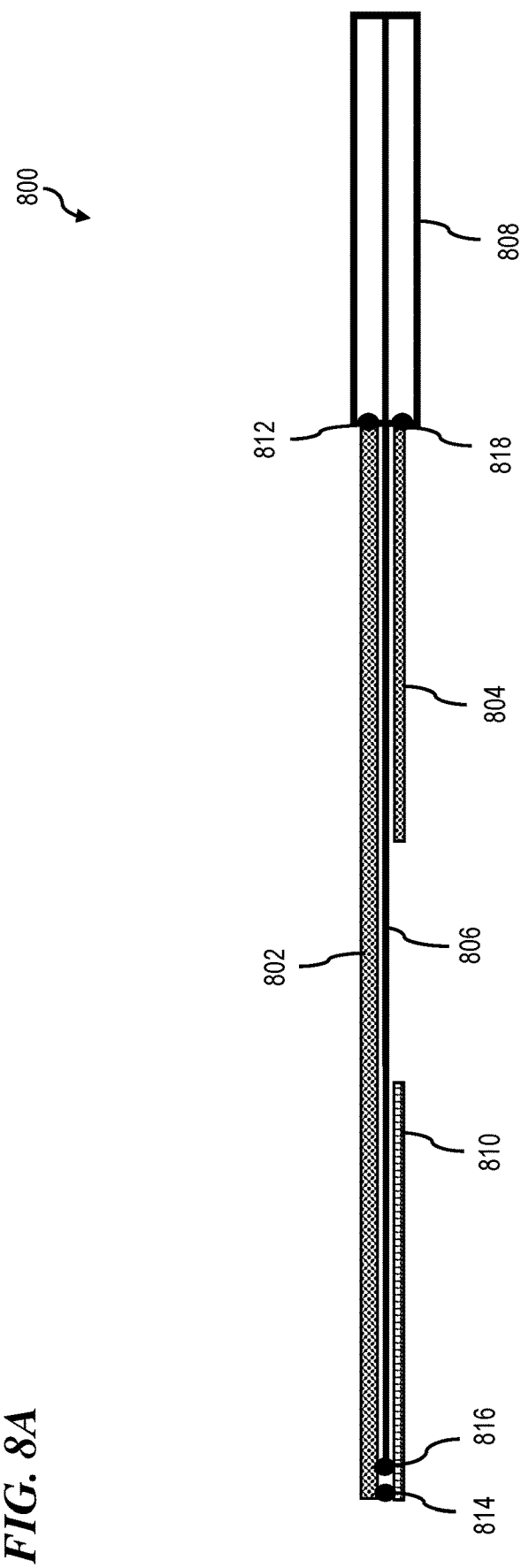
FIG. 8A is a schematic diagram showing a deflection mechanism 800, according to one embodiment of the present invention.

FIG. 8A is a schematic diagram showing a deflection mechanism 800 with expandable constraints, according to one embodiment of the present invention. Deflection mechanism 800 is shown in a non-deflected or neutral state in FIG. 8A. In some embodiments, deflection mechanism 800 includes a deflecting beam 802. In some embodiments, pull wire 806 is attached to beam 802 on a distal end of beam 802 at joint 816. In some embodiments, hypodermic tube 808 is attached to beam 802 on a proximal end of beam 802 at joint 812. In some embodiments, a first shorter beam 810 is attached to deflecting beam 802 at its distal end by joint 814 so that pull wire 806 is positioned between beam 802 and first shorter beam 810 as shown in FIG. 8A. In some embodiments, a second shorter beam 804 is attached to the proximal end of beam 802 at the juncture with the hypodermic tube 808 by joint 818 so that pull wire 806 is positioned between deflecting beam 802 and first and second shorter beams 810 and 804.

Figure 8B:
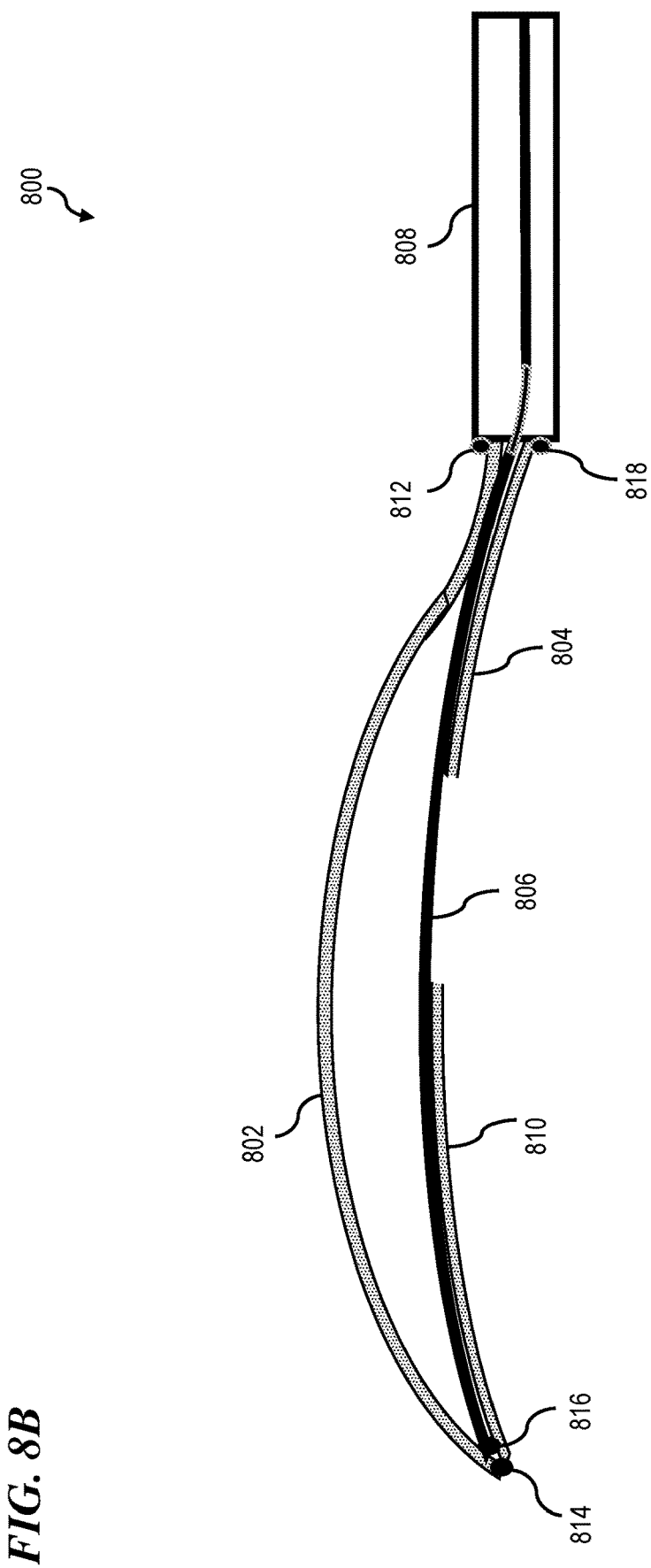
FIG. 8B is a schematic diagram of deflection mechanism 800 in a tensioned state, according to one embodiment of the present invention.

FIG. 8B is a schematic diagram of deflection mechanism 800 in a tensioned state, according to one embodiment of the present invention. In some embodiments, as pull wire 806 is tensioned, beam 802 curves in response to the shortening of the distance of the exposed pull wire 806 between points 814 and 812. Tension in pull wire 806 causes wire 806 to straighten and form a chord to the arc defined by the fixed points 814 and 812 as shown in FIG. 8B. However, as pull wire 806 moves away from beam 802, it encounters first and second shorter beams 810 and 804 which resists the lateral movement of pull wire 806 away from deflecting beam 802. In some embodiments, the effect of the resistance of the two smaller beams 810 and 804 is to modify the geometry of pull wire 806 so that it forms an arc with a larger radius curvature than that of beam 802 as shown in FIG. 8B. The two smaller beams 810 and 804 act to limit expansion of pull wire 806, i.e., constrain movement of pull wire 806 away from beam 802. In some embodiments, the structural properties of the two smaller beams 810 and 804 are designed to change the geometric shape of pull wire 806 to prevent pull wire 806 from becoming a geometric chord of the deflected arc represented by beam 802. In some embodiments, in the case where the constraining beams 810 and 804 are highly flexible, the shape of pull wire 806 will approach that of a chord of the beam arc, which allows the maximum possible movement of pull wire 806 away from the deflection beam 802. In other embodiments, in the case where the constraining beams 810 and 804 are stiffer, the shape of pull wire 806 approaches that of beam 802 itself. Ultimately, in some embodiments, a stiffness will be reached at which the effect of constraining beams 810 and 804 is identical to that of a lumen of a catheter shaft into which a deflection mechanism has been placed, effectively negating the benefits of constraining beams 810 and 804.

In one embodiment of the current invention for a device used for esophageal deflection, the deflecting beam 802 is made of one or more metals which have high yield strength and high hardness. In some embodiments, the yield strength is between 100,000 and 300,000 pounds per square inch (psi), in some embodiments, between 175,000 and 200,000 psi, in some embodiments, between 200,000 and 225,000 psi. In some embodiments, the metal hardness of deflecting beam 802 is between RC30 and RC60 (as used herein, the "RC" hardness refers to the Rockwell scale for hardness also known as "HRC"; see, e.g., https://en.wikipedia.org/wiki/Rockwell scale), in some embodiments, between RC45 and RC55, in some embodiments, between RC50 and RC55. In some embodiments, beam 802 material thickness ranges from 0.002 inches to 0.050 inches, in some embodiments, from 0.005 inches to 0.025 inches, in some embodiments, from 0.010 inches to 0.020 inches. In some embodiments, beam 802 widths range from 0.050 inches to 0.500 inches, in some embodiments, from 0.100 inches to 0.250 inches, in some embodiments, from 0.150 to 0.200 inches. In some embodiments, beam 802 lengths range from 3.0 inches to 20.0 inches, in some embodiments, from 5.0 inches to 10 inches, in some embodiments, from 6.0 inches to 9.0 inches.

In some embodiments, for other applications that deflect a body lumen where the deflecting forces are lower, beam 802 is made from plastic materials that typically have lower yield strengths and lower hardness. In some embodiments, plastic materials such as nylon, polyester and Teflon® are within the scope of the present invention for beam 802.

In other embodiments of the present invention of a deflection mechanism with expandable constraints, the design of the constraint mechanism can be categorized as follows: namely, continuous, segmented or balloon-based. In some embodiments of a continuous design there is a single structural element surrounding beam 802 along its entire length, i.e., it extends to at least from its distal end to at least its proximal end (see, e.g., FIGS. 9A, 10A, 11A, 12A, and 17). In some embodiments, the continuous structural element is expandable (see, e.g., FIGS. 9A, 10A, and 17), a property which allows the constraint to change its diameter during beam deflection, or rigid (see, e.g., FIGS. 11A and 12A), a property which fixes the diameter of the constraint to a predetermined, fixed value. In some embodiments of a segmented design, selected constraining elements are affixed to beam 802 at various locations along beam 802 to constrain pull wire 806 at discrete locations along beam 802 (see, e.g., FIG. 8A, FIG. 13A, FIG. 14A, and FIG. 15A). In some embodiments, the segmented constraints are expandable (see, e.g., FIG. 14A), which allows a change in physical size during deflection, or a fixed size (see, e.g., FIG. 15A) similar to the continuous design. In some embodiments of a balloon-based design, the constraints are incorporated into a deflection catheter which contains the deflection mechanism, and in some such embodiments, the constraints are incorporated into the balloon(s) of a deflection catheter (see, e.g., FIG. 18) or as an additional material affixed to the balloon(s) (see, e.g., FIG. 16). Each of these designs will be discussed in more detail forthwith.

Figure 9A:
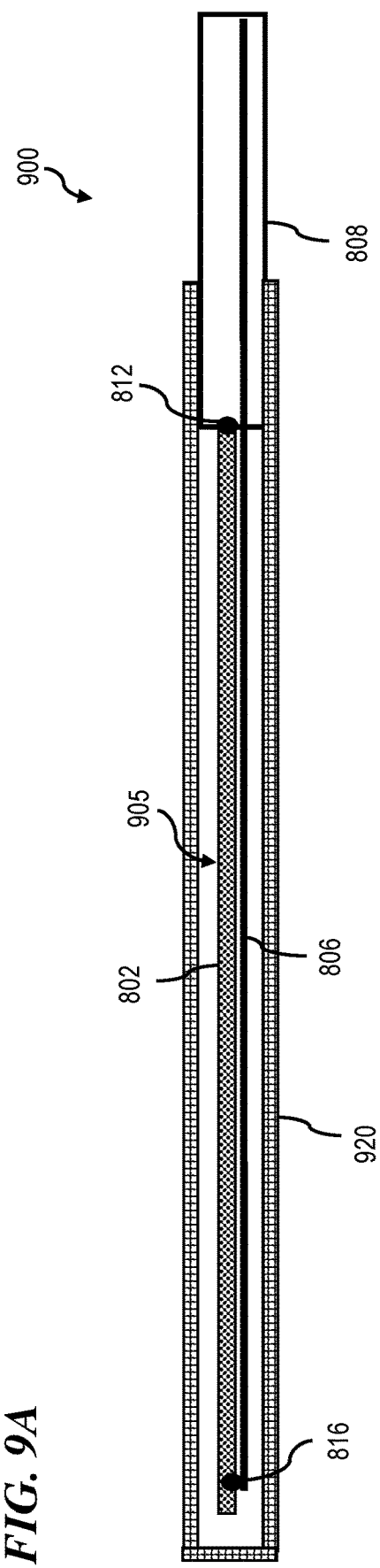
FIG. 9A is a schematic diagram of a deflection assembly 900, according to one embodiment of the present invention.

FIG. 9A is a schematic diagram of a deflection assembly 900, according to one embodiment of the present invention. In some embodiments, deflection assembly 900 includes a continuous elastic constraint. In this design, deflection assembly 900 is comprised of a deflection mechanism 905 which is surrounded by elastic tube 920 which can stretch radially as pull wire 806 moves laterally away from beam 802.

Figure 9C:
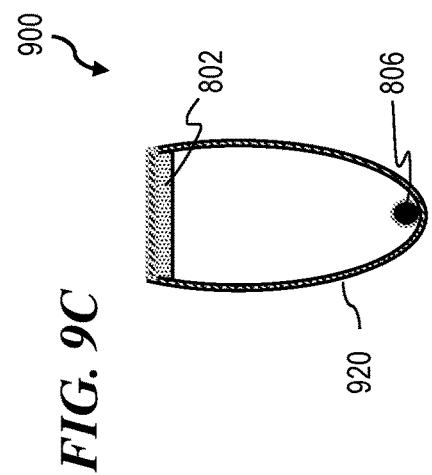
FIG. 9C is a cross-sectional view of deflection assembly 900 as viewed toward the right-hand side of FIG. 9A from the middle of deflection assembly 900, with beam 802 in its deflected state and pull wire 806 moved laterally away from beam 802, according to one embodiment of the present invention.
Figure 9B:
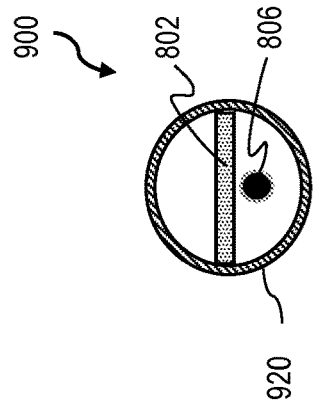
FIG. 9B is a cross-sectional view of deflection assembly 900 as viewed toward the right-hand side of FIG. 9A from the middle of deflection assembly 900, with beam 802 in its neutral or undeflected state, according to one embodiment of the present invention.

FIG. 9B is a cross-sectional view of deflection assembly 900 as viewed toward the right-hand side of FIG. 9A from the middle of deflection assembly 900, with beam 802 in its neutral or undeflected state, according to one embodiment of the present invention.

FIG. 9C is a cross sectional view of deflection assembly 900 as viewed toward the right-hand side of FIG. 9A from the middle of deflection assembly 900, with beam 802 in its deflected state and pull wire 806 moved laterally away from beam 802, according to one embodiment of the present invention. In some embodiments, the materials and tube wall thickness are selected to provide the desired distance of pull wire 806 from beam 802 at its maximum desired deflection. In some embodiments, constraint tubes 920 with thinner walls made of a lower-durometer material will allow more expansion of pull wire 806 away from beam 802 whereas tubes 920 with thicker walls made of higher-durometer materials will limit the expansion of pull wire 806 away from beam 802.

In some embodiments of the present invention, tube 920 is made of silicone, polyurethane, latex or any plastic material which stretches easily when force is applied. In some embodiments, material durometers of tube 920 range from 10A to 90A, in some embodiments, from 20A to 60A and in some embodiments, from 40A to 50A. In some embodiments, material wall thicknesses of tube 920 range from 0.001 inches to 0.050 inches, in some embodiments, from 0.005 to 0.030 inches and in some embodiments, from 0.010 inches to 0.020 inches.

Figure 10A:
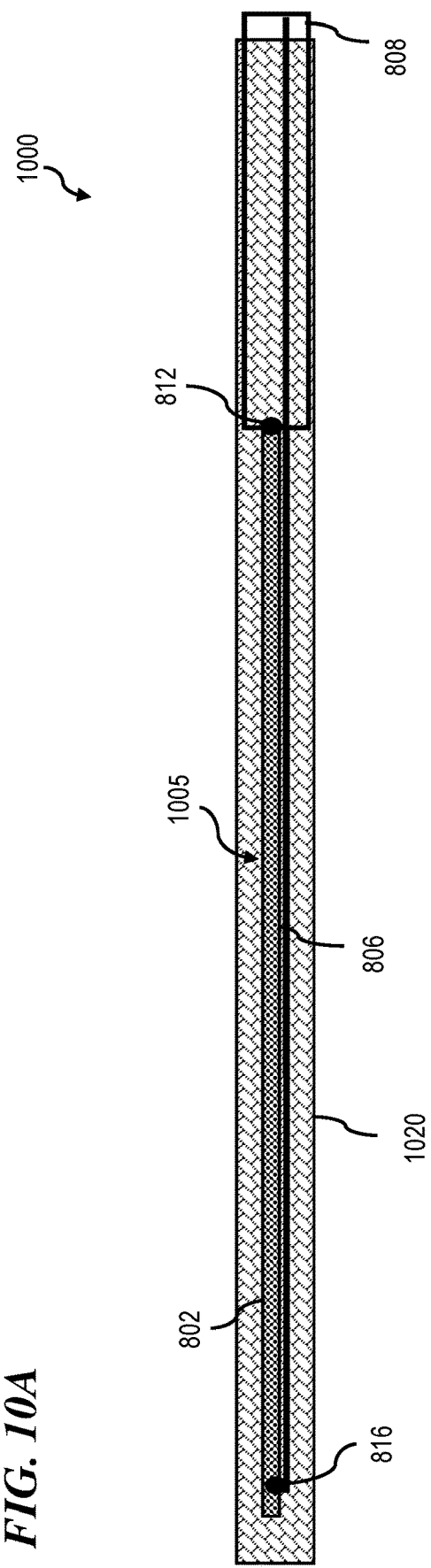
FIG. 10A is a schematic diagram of a deflection assembly 1000, according to one embodiment of the present invention.
Figure 10C:
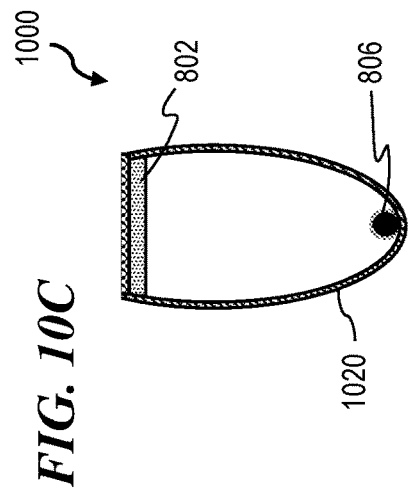
FIG. 10C is a cross-sectional view of deflection assembly 1000 as viewed toward the right-hand side of FIG. 10A from the middle of deflection assembly 1000, with beam 802 in its deflected state and pull wire 806 moved laterally away from beam 802, according to one embodiment of the present invention.
Figure 10B:
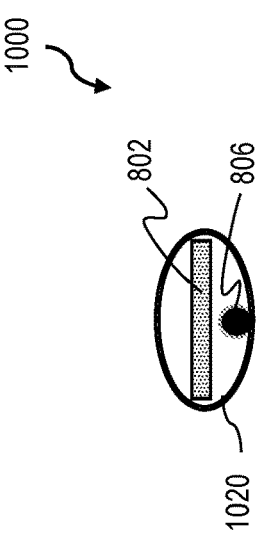
FIG. 10B is a cross-sectional view of deflection assembly 1000 as viewed toward the right-hand side of FIG. 10A from the middle of deflection assembly 1000, with beam 802 in its neutral or undeflected state, according to one embodiment of the present invention.

FIG. 10A is a schematic diagram of a deflection assembly 1000, according to one embodiment of the present invention. In some embodiments, deflection assembly 1000 includes a continuous elastic constraint. In some embodiments of this design, deflection assembly 1000 is comprised of deflection mechanism 1005 which is surrounded by wire mesh 1020 having a braided, woven or knitted material construction. In some embodiments, mesh 1020 is designed to expand to a fixed diameter beyond which expansion is no longer possible. In some embodiments of esophageal deflection, the maximum diameter of mesh 1020 is fixed at the largest esophageal diameter of approximately 2.5 cm. Depending on the structure of wire mesh 1020, in some embodiments mesh 1020 foreshortens longitudinally as it expands radially as is the case with braiding. To accommodate this foreshortening, in some embodiments, mesh 1020 extends proximally along the body of the deflection mechanism, the extension length being determined as a multiple of the distance the mesh 1020 foreshortens at its maximum beam deflection. During deflection of beam 802, the lateral movement of pull wire 806 expands mesh 1020 from its initially circular shape as shown in the cross-sectional view of FIG. 10B to an ellipsoidal shape as shown in the cross-sectional view of FIG. 10C, and at that point mesh 1020 has reached its maximum design diameter, mesh 1020 no longer expands, and thus the lateral movement of pull wire 806 away from beam 802 is constrained to this maximum value.

FIG. 11A is a schematic diagram of a deflection assembly 1100, according to one embodiment of the present invention. In some embodiments, deflection assembly 1100 includes a continuous constraint. In some embodiments of FIG. 11A, deflection assembly 1100 is comprised of a deflection mechanism 1105 surrounded by a spring 1120 of a predetermined diameter that is attached to hypodermic tube 808 at joint 1115. In some embodiments, spring 1120 is tightly wound such that adjacent coils touch each other, or loosely wound so that a space exists between each coil. The space between the coils can be a constant dimension along the entire length of the coil or can vary along its length. For example, in some embodiments it is advantageous to have a larger spacing in the center region of the beam to permit easier bending of beam 802 in that region. In some embodiments, the distal end of spring 1120 is such that the distal end of beam 802 is free to float inside the spring 1120. For the spring 1120, the ID (inner diameter) of spring 1120 is determined by the desired expansion ratio (ER) for a corresponding deflection catheter. In some embodiments, one consideration for the OD (outer diameter) of spring 1120 is that it must be smaller than the ID of a corresponding deflection catheter (e.g., a balloon catheter) in order to accommodate placement of deflection assembly 1100 therein.

In operation, in some embodiments, pull wire 806 is very close to beam 802 when beam 802 is in its straight configuration, as shown in FIG. 11B. In some embodiments, as shown in FIG. 11C, when beam 802 is deflected (and thus spring coil 1120 is deflected), pull wire 806 moves to the inside wall of spring coil 1120, along the convex internal surface of spring coil 1120, but the position of deflected beam 802 within spring coil 1120 as viewed in FIG. 11C remains substantially unchanged from the position of the straight beam 802 within spring coil 1120 shown in FIG. 11B.

Figure 12A:
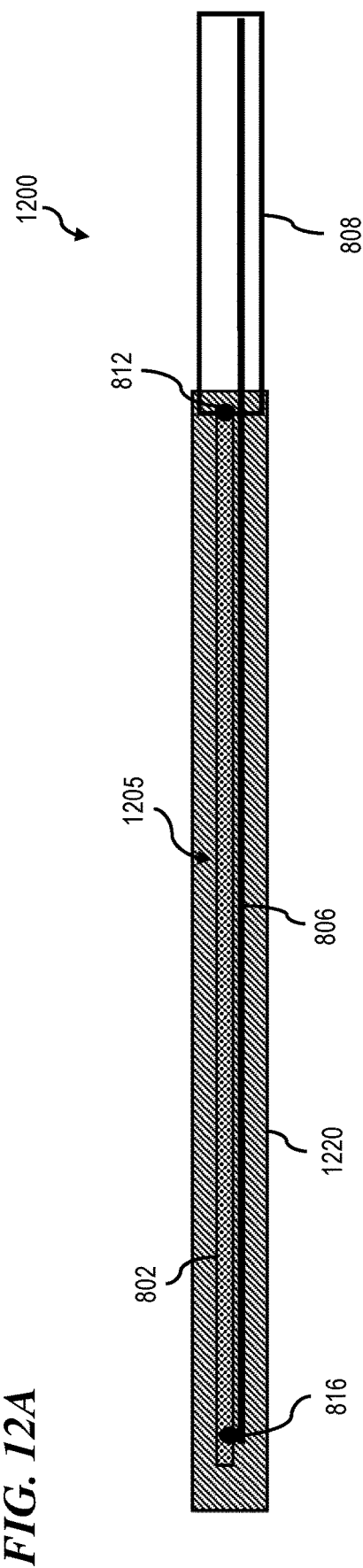
FIG. 12A is a schematic diagram of a deflection assembly 1200, according to one embodiment of the present invention.
Figure 12C:
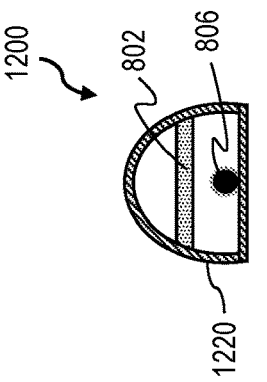
FIG. 12C is a cross-sectional view of deflection assembly 1200 as viewed toward the right-hand side of FIG. 12A from the middle of deflection assembly 1200, with beam 802 in its deflected state and pull wire 806 moved laterally away from beam 802, according to one embodiment of the present invention.
Figure 12D:
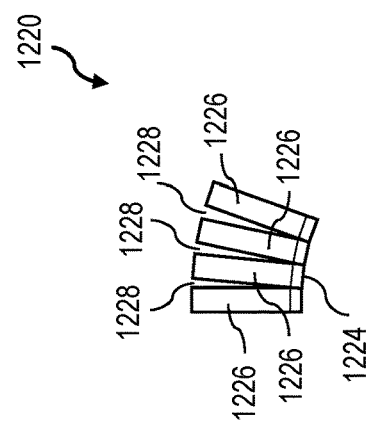
FIG. 12D is a magnified cross-sectional view of a portion of plastic tube 1220 showing segments 1226 and cuts 1228, according to one embodiment of the present invention.
Figure 12B:
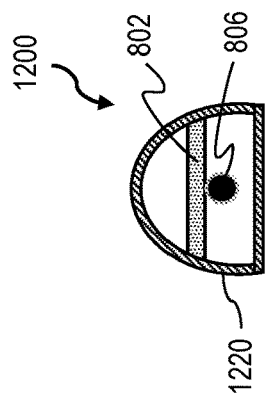
FIG. 12B is a cross-sectional view of deflection assembly 1200 as viewed toward the right-hand side of FIG. 12A from the middle of deflection assembly 1200, with beam 802 in its neutral or undeflected state, according to one embodiment of the present invention.

FIG. 12A is a schematic diagram of a deflection assembly 1200, according to one embodiment of the present invention. In some embodiments, deflection assembly 1200 includes a continuous fixed constraint. This design is similar to that shown in FIG. 11A with the exception that spring coil 1120 is replaced by a plastic tube 1220 with perpendicular cuts partially through its diameter, and plastic tube 1220 surrounds a deflection mechanism 1205. In some embodiments of FIG. 12A, deflection assembly 1200 is comprised of deflection mechanism 1205 which is surrounded by plastic tube 1220 which has been shaped into a cross sectional geometry of a letter "D" as shown in FIG. 12B. In some embodiments, plastic tube 1220 contains cuts perpendicular to its longitudinal axis starting at the outer perimeter of the "D" and extending to but not penetrating through the inner edge 1224 of the "D" shape. As shown in FIG. 12D, the resulting segments 1226 are separated by cuts 1228 and connected to the inner edge 1224 to form a continuous plastic structure, the bottom of which serves as a hinge connecting all sliced segments 1226 of the plastic tube 1220 to form a single entity.

In operation, in some embodiments, pull wire 806 will lie very close to beam 802 when beam 802 is in its neutral or straight configuration, as shown in FIG. 12B. In some embodiments, as shown in FIG. 12C, when beam 802 is deflected (and thus plastic tube 1220 is deflected), pull wire 806 moves to the inside surface of the flat part of the "D"-shape, but the position of deflected beam 802 within plastic tube 1220 as viewed in FIG. 12C remains substantially unchanged from the position of the straight beam 802 within plastic tube 1220 shown in FIG. 12B. The inside surface of the flat part of the "D" shape then acts as a constraint for pull wire 806 while the top of the "D"-segments expands in order to minimize the forces required to deflect the constraint tube 1220.

Another set of embodiments of a deflection mechanism with expandable constraints according to the present invention can be classified as segmented designs in which constraining elements are affixed to beam 802 at selected locations along beam 802 to limit the movement of pull wire 806 at discrete locations along beam 802. In some embodiments, the constraints are expandable; in other embodiments, the constraints have a fixed diameter in the same manner as those of a continuous constraint design.

Figure 13A:
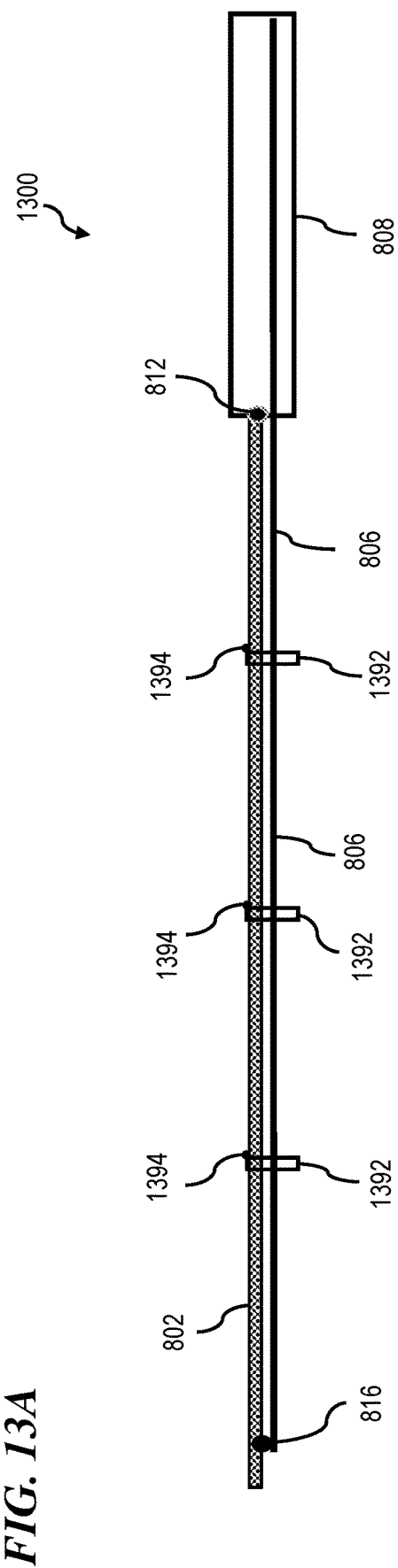
FIG. 13A is a schematic diagram of a deflection assembly 1300 in a neutral or undeflected state, according to one embodiment of the present invention.
Figure 13C:
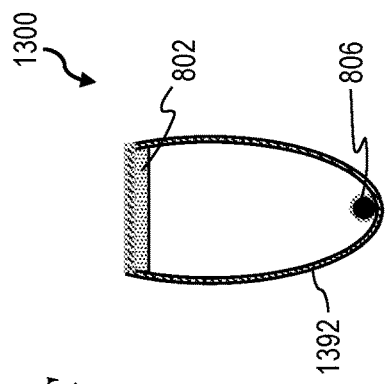
FIG. 13C is a cross-sectional view of deflection assembly 1300 as viewed toward the right-hand side of FIG. 14A from the middle of deflection assembly 1300, with beam 802 in its deflected state and pull wire 806 moved laterally away from beam 802, according to one embodiment of the present invention.
Figure 13B:
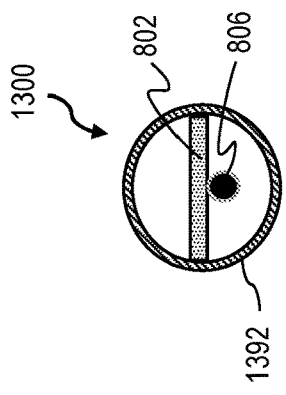
FIG. 13B is a cross-sectional view of deflection assembly 1300 as viewed toward the right-hand side of FIG. 13A from the middle of deflection assembly 1300, with beam 802 in its neutral or undeflected state, according to one embodiment of the present invention.
Figure 13D:
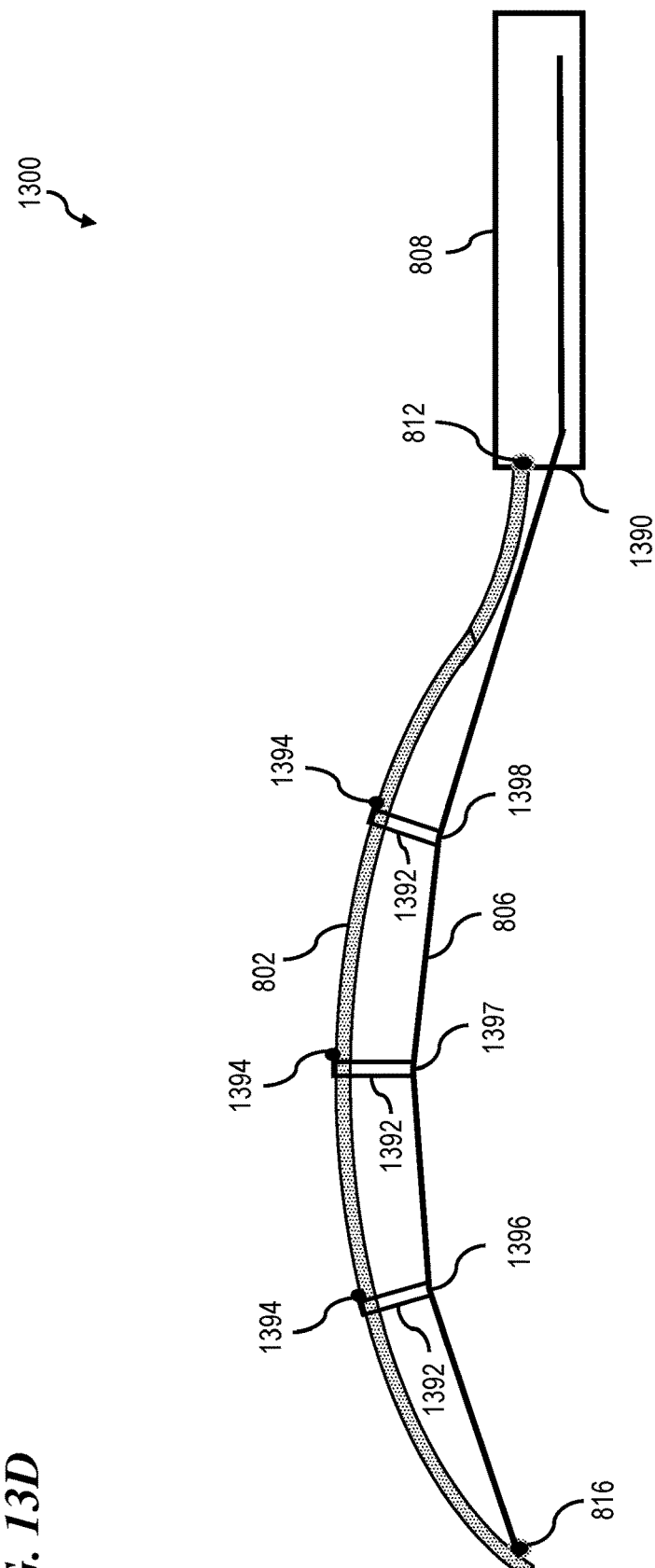
FIG. 13D is a schematic diagram of deflection assembly 1300 in its deflected state, according to one embodiment of the present invention.

FIG. 13A is a schematic diagram of a deflection assembly 1300 in a neutral or undeflected state, according to one embodiment of the present invention. In some embodiments, deflection assembly 1300 includes a segmented expandable constraint. In some embodiments of deflection assembly 1300, rings 1392 of circular material are placed over beam 802 and their position fixed to beam 802 by joint 1394 by using standard methods to join metals such as adhesives, spot welding, etc. In this concept, rings 1392 are similar to the continuous constraint designs discussed previously except that discrete rings 1392 of material are used at defined axial locations along deflection beam 802. Similar to the choice of materials for a continuous constraint, rings 1392 of a segmented constraint can be elastic or rigid. In some embodiments, for an elastic constraint, rings 1392 are made of soft plastics with a tubular cross section similar to that shown in FIG. 13B, which is similar to the cross section of a continuous constraint shown in FIG. 9A. In some embodiments, when pull wire 806 is tensioned, the circular shape is deformed into an elongated structure allowing pull wire 206 to move away from beam 802, as shown in FIG. 13C, which is similar to FIG. 9C. In operation, pull wire 806 now becomes a series of chords connected at each of the support points as shown in FIG. 13D. Pull wire 806 forms chords between points 816 and 1396, points 1396 and 1397, 1897 and 1398, and 1398 and the end of the support tube at point 1390. This contrasts with the continuous arc formed by assembly 900 of FIG. 9A, which uses a continuous elastic constrain.

Another embodiment of deflection assembly with an expandable constraint according to the present design is shown in FIGS. 14A-14C. FIG. 14A is a cross-sectional view of a deflection assembly 1401 with beam 802 in its neutral or undeflected state, according to one embodiment of the present invention. In some embodiments, segmented expandable constraints 1410 comprised of rings are made of spring wire shaped into multiple loops as shown in FIG. 14A. In some embodiments, the wire loop 1410 is fastened to the underside of beam 802 with pull wire 806 passing through the inside of the loop.

FIG. 14B is a cross-sectional view of deflection assembly 1401 with beam 802 in its deflected state and pull wire 806 moved laterally away from beam 802, according to one embodiment of the present invention. In some embodiments, the wire loop 1410 is designed so that it can expand in diameter as pull wire 806 moves away from beam 802 and exerts a downward force on the loop 1410 opposite beam 802. In some embodiments, the amount of expansion is controlled by the structural stiffness of the wire used to form the loop 1410 which is a function of its diameter and modulus of elasticity.

FIG. 14C is a cross-sectional view of a deflection assembly 1402 with beam 802 in its deflected state and pull wire 806 moved laterally away from beam 802, according to one embodiment of the present invention. In some embodiments, stops 1415 are placed on the ends of the wires of wire loop 1410 such that the wire loop 1410 can only expand until stops 1415 engage each other at the bottom of the loop as shown in FIG. 14C.

Figure 15B:
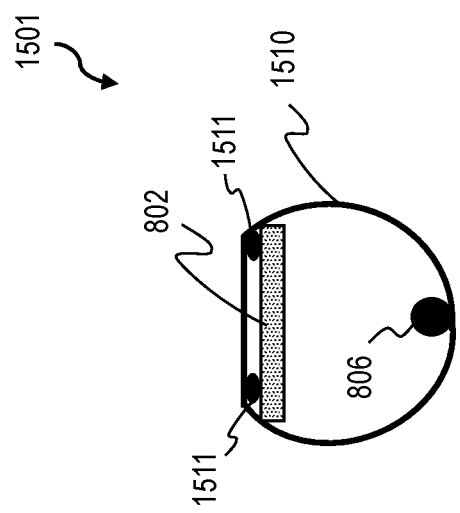
FIG. 15B is a cross-sectional view of deflection assembly 1501 with beam 802 in its deflected state and pull wire 806 moved laterally away from beam 802, according to one embodiment of the present invention.
Figure 15A:
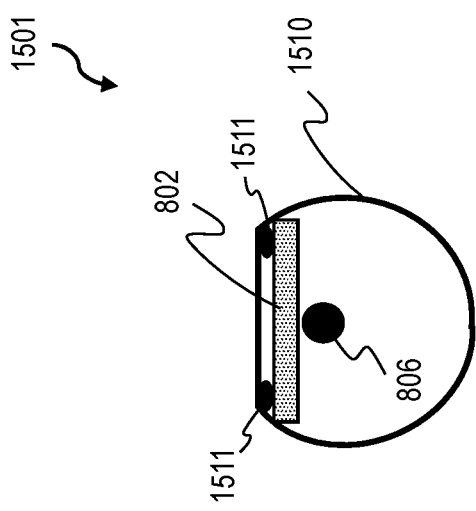
FIG. 15A is a cross-sectional view of a deflection assembly 1501 with beam 802 in its neutral or undeflected state, according to one embodiment of the present invention.

FIG. 15A is a cross-sectional view of a deflection assembly 1501 with beam 802 in its neutral or undeflected state, according to one embodiment of the present invention. In some embodiments, segmented fixed constraints comprised of rings 1510 are made of a rigid material similar to the materials used in a continuous constraint embodiment. In some embodiments, as shown in FIG. 15A and FIG. 15B, ring 1510 has a flat section at its interface with the top side of beam 802. In some embodiments, ring 1510 is fastened to beam 802 using an adhesive or solder 1511 or other joining methods compatible with the metal composition of the materials involved. In some embodiments, in operation, the diameter of ring 1510 does not change between the neutral, non-deflected state of beam 802 (FIG. 15A) to that of the deflected state beam 802 (FIG. 15B). However, in the neutral state (FIG. 15A), pull wire 806 resides in proximity to beam 802, while in the deflected state (FIG. 15B) pull wire 806 resides closer to the inside surface of ring 1510 opposite beam 802. In some embodiments, the main advantage of this design is that segmentation allows the rigid elements to physically move relative to each other, reducing or eliminating the rigidity of the constraint material itself, thus not increasing the stiffness of the beam assembly.

Figure 16:
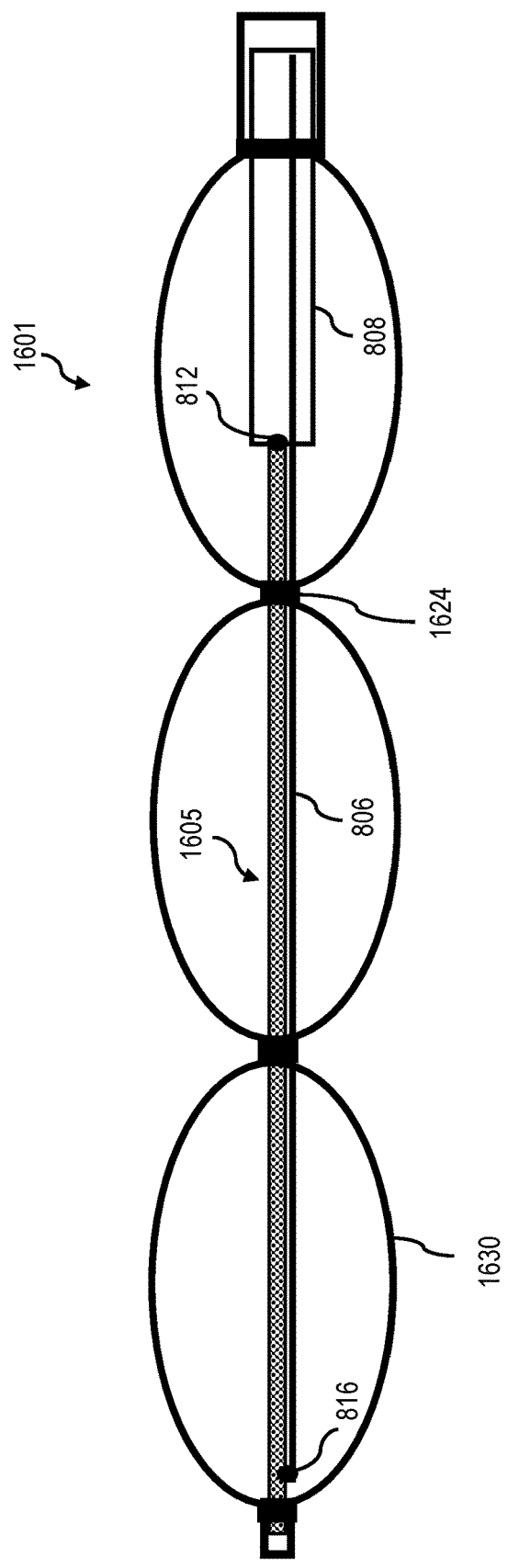
FIG. 16 is a schematic diagram of a deflection assembly 1601, according to one embodiment of the present invention.

FIG. 16 is a schematic diagram of a deflection assembly 1601, according to one embodiment of the present invention. In some embodiments, deflection assembly 1601 incorporates segmented constraints into an elastic member 1630, which encapsulates the deflection mechanism 1605. In some embodiments, elastic member 1630 is part of an outer deflection catheter into which the deflection mechanism 1605 is inserted. In one embodiment, elastic member 1630 is a balloon which is inflated to expand the lumen into which deflection mechanism 1605 is placed. In some embodiments, elastic member 1630 has sections of increased wall thickness in certain axial segments along the length of the deflection mechanism. FIG. 16 shows elastic member 1630 as a balloon in which the thickened necks act as constraints. In some embodiments, this is accomplished by making the neck regions with a thicker material or adding another, separate layer of material 1624 to the outside of the balloon as shown in FIG. 16. In some embodiments, ring material 1624 is elastic (in other embodiments, ring material 1624 is rigid). In some embodiments of the elastic design, the thickened band 1624 is incorporated into the balloon during the balloon blowing process, in which case the balloon is a single entity with varying wall thickness. In another embodiment, an elastic material 1624 is added over the balloon material once the multi-lobed balloon is mounted. In another embodiment, rings 1624 are made of a rigid material with one side of ring 1624 bonded to the balloons with an adhesive. In some embodiments, rigid bands 1624 are made of a radiopaque material that is visible during fluoroscopy, which is a useful property for determining the location of the deflected section of the catheter relative to other body structures such as the posterior wall of the heart during ablation for treatment of atrial fibrillation.

Figure 17:
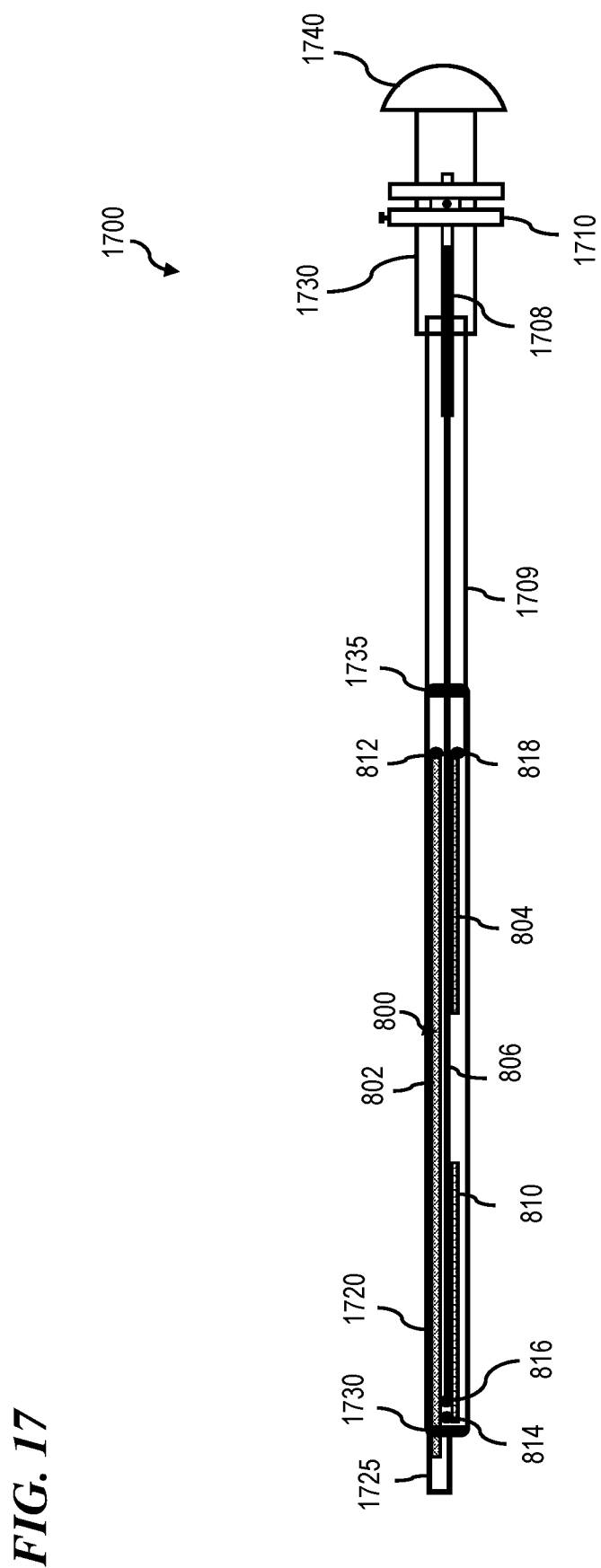
FIG. 17 is a schematic diagram of a deflection assembly 1700, according to one embodiment of the present invention.

FIG. 17 is a schematic diagram of a deflection assembly 1700, according to one embodiment of the present invention. In some embodiments, deflection assembly 1700 is suitable for deflecting a body lumen in a clinical setting and includes expandable constraints. In some embodiments, the distal end of deflection assembly 1700 is comprised of deflection mechanism 800, illustrated in detail in FIG. 8, and sheath 1720 which encapsulates the deflection mechanism 800 to seal the mechanism from fluid infiltration and to protect a body lumen from damage from elements of the deflection device. In some embodiments, sheath tubing 1720 is made from a thin-walled silicone tube of a diameter approximately that of shaft 1709. In some embodiments, wall thicknesses of sheath 1720 range from 0.0005 inches to 0.050 inches, in some embodiments, from 0.003 inches to 0.015 inches, in some embodiments, from 0.005 inches to 0.010 inches, in some embodiments, approximately 0.005 inches. Alternatively, in some embodiments, sheath 1720 is made from a tube of a low-durometer material such as polyurethane, nylon, polyester, rubber latex or copolymers of these materials such as C-Flex®. In some embodiments, sheath 1720 is bonded to shaft 1709 at joint 1735 using an adhesive compatible with the materials of the shaft 808 and sheath tubing 1720. Similarly, in some embodiments, at the distal end of the deflection device, tube 1725 is bonded to sheath 1720 with adhesive joint 1730 using an adhesive similar to that of joint 1735. In some embodiments, the proximal end of deflection device 1700 includes a handle 1730 and sliding knob 1710 for tensioning/locking the position of the pull wire to deflect a body lumen during a procedure. In some embodiments, knob 1710 is slidably coupled to handle 1730, and, in some embodiments, knob 1710 includes set screw 1740 for the locking the position of the knob relative to the handle 1730 to fix the shape of the deflection mechanism once the desired degree of deflection is attained. In some embodiments, hypodermic tube 1708 interoperably couples pull wire 806 with knob 1710 so that any axial movement of the knob 1710 is translated into comparable movement of pull wire 806 for purposes of changing the degree of lateral movement of the deflection mechanism.

In one embodiment, a deflection device which contains a deflection mechanism with expandable constraint such as deflection assembly 1700 is used to deflect an esophagus in a cardiac ablation procedure for treatment of atrial fibrillation. In this procedure, deflection device 1700 is placed in the mouth of the patient and the distal end of the device passed through the throat into the esophagus and positioned at the desired location within the esophagus. Once positioned, the slide knob 1710 is moved axially to curve the deflection device, thereby translating the esophagus consistent with the curvature of the deflection mechanism. If the location of the deflection is not oriented with respect to thoracic cavity or relevant cardiac structures as desired, the deflection mechanism is returned to its neutral state, the deflection device rotated in the esophagus to the desired orientation and the deflection mechanism curved using the slide knob on the handle. Once the desired orientation and degree of curvature are obtained, the position of the knob 1710 on the handle 1730 is locked using set screw 1740 and a cardiac ablation procedure is performed. Upon completion of the procedure, the knob 1710 on the handle 1730 is released, the deflection device returned to its neutral position and the deflection device retracted from the esophagus.

Figure 18:
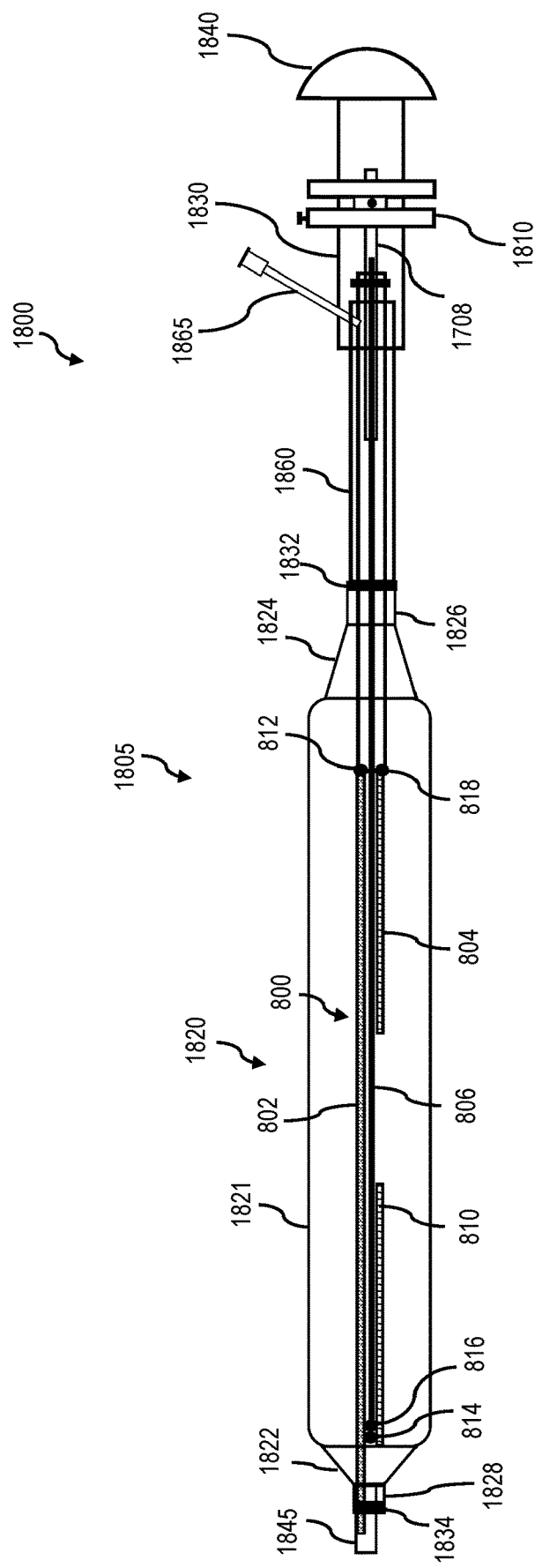
FIG. 18 is a schematic diagram of a deflection assembly 1800, according to one embodiment of the present invention.

FIG. 18 is a schematic diagram of a deflection assembly 1800, according to one embodiment of the present invention. In some embodiments, deflection assembly 1800 is for use in a clinical setting and uses a deflection mechanism with expandable constraints. In some embodiments, deflection assembly 1800 is comprised of deflection mechanism 800, illustrated in detail in FIG. 8, which is surrounded by balloon catheter 1805. In some embodiments, balloon catheter 1805 includes balloon 1820, which encapsulates deflection mechanism 800, catheter shaft 1860, which is operably coupled to balloon 1820, and handle 1830, which operably couples to deflection mechanism 800 and balloon 1820. In some embodiments, balloon 1820 is made of a thin sheet of 90A durometer polyurethane. In some embodiments, wall thicknesses of balloon 1820 range from 0.0005 inches to 0.050 inches, in some embodiments, from 0.001 inches to 0.015 inches, in some embodiments, from 0.001 inches to 0.005 inches, and in some embodiments, approximately 0.0025 inches. In some embodiments, a sheet of polyurethane is formed into balloon 1820 with a cylindrical section 1821 at its center, with cones 1822 and 1824 on each end that taper to form necks 1826 and 1828, which interface with the shaft 1860 of balloon catheter 1805. In some embodiments, the diameter of the cylindrical part 1821 of the balloon 1820 is selected as the desired diameter of the inflated balloon 1820 in a clinical setting. In some embodiments, the diameter ranges from 0.125 inches to 1.5 inches or in some embodiments, from 0.375 to 1.0 inches or in some embodiments, between 0.65 and 0.75 inches when inflated. Alternatively, in some embodiments, balloon 1820 is made from an extruded tube of a desired material and the tube heated and blown into a mold with the desired balloon shape. In some embodiments, other durometer polyurethane materials are used ranging from 10 Shore A thru 95 Shore A and from 50 Shore D to 70 Shore D. Alternatively, in some embodiments, more-compliant balloons 1820 are designed with a lower- or softer-durometer material such as in the range 10 Shore A to 30 Shore A which allows the balloon dimeter to be changed at the time of a procedure by increasing fluid pressure within the balloon. Alternatively, in some embodiments, non-compliant balloons 1820 are designed using materials in the range 30 to 70 Shore D, the use of which implies the diameter cannot be changed during a clinical procedure. The use of 90 Shore A as the base material gives the balloon 1820 a semi-compliant characteristic, which means that the diameter can be changed during a procedure if sufficient pressure is applied to cause stretching of the balloon material. Alternatively, in some embodiments, balloon 1820 is made from other materials which have the desired range of durometers, such as silicone, latex rubber, nylon, polyester or copolymers of these materials such as C-Flex®. In some embodiments, balloon 1820 is bonded to catheter shaft 1860 using neck joint 1832 with an adhesive compatible with the materials of the shaft and balloon. Similarly, in some embodiments, at the distal end of balloon catheter 1805, tube 1845 is bonded to neck 1828 with adhesive joint 1834 using an adhesive similar to that of joint 1832. In some embodiments, the proximal end of balloon catheter 1805 includes a handle 1830, sliding knob 1810 for tensioning/locking the pull wire and a port for inflation/deflation of the balloon similar to that of the deflection device shown in FIG. 17 (e.g., in some embodiments, knob 1810 includes set screw 1840 for the locking the position of the knob 1810 relative to the handle 1830 to fix the shape of the deflection mechanism once the desired degree of deflection is attained). Additionally, in some embodiments, tube 1865 is attached to handle 1830 and is operably coupled to balloon 1820 for purposes of inflating and deflating the balloon 1820.

In some embodiments, deflection assembly 1800 is used to deflect an esophagus in a cardiac-ablation procedure for treatment of atrial fibrillation. In some embodiments of this procedure, a vacuum is pulled on the inside of the deflection assembly 1800 using a syringe and side port 1865 with Luer, after which balloon 1820 is wrapped tightly around the deflection mechanism 800. In some embodiments, the deflection assembly 1800 is placed in the mouth of the patient and the distal end of the device passed through the throat and into the esophagus and positioned at the desired location in the esophagus. The balloon 1820 is then inflated with a fixed volume of a saline/contrast agent to expand the esophagus to a larger diameter in order to tighten the esophagus for purposes of visualization and ease of displacement. Once positioned, the knob 1810 on the handle 1830 is used to curve the deflection device which translates the esophagus in the same direction as the curvature of the deflection mechanism 800. If the plane of deflection is not oriented correctly with respect to the thoracic cavity or relevant cardiac structures, the deflection mechanism 800 is returned to its neutral state, the deflection device is then rotated to the desired position within the inflated balloon 1820 and the deflection mechanism 800 curved once again using the slide knob 1810 on the handle 1830. Once the desired orientation and degree of curvature is obtained, the position on the knob 1810 on the handle 1830 is locked and a cardiac ablation procedure performed. After completion of a procedure, the knob 1810 on the handle 1830 is unlocked, the deflection mechanism 800 within the balloon catheter 1805 returned to its neutral position, the balloon 1820 deflated by extracting fluid from the balloon and the balloon catheter 1805 retracted from the esophagus.

In some embodiments, the present invention provides a deflection system for deflecting a body lumen that includes a deflection mechanism, wherein the deflection mechanism includes: a beam having a proximal end and a distal end, wherein the beam includes a neutral position and a deflected position, a pull wire coupled to the distal end of the beam, wherein the beam is configured to be placed in the deflected position when a tension force is applied to the pull wire, and wherein at least a portion of the pull wire is configured to move to a displacement distance away from the beam when the tension force is applied to the pull wire, and one or more constraint members operatively coupled to the beam, wherein each one of the one or more constraint members is configured to limit the displacement distance of the pull wire from the beam when the tension force is applied to the pull wire.

In some embodiments of the system, the deflection mechanism further includes: a tubular support member coupled to the proximal end of the beam, wherein the pull wire is configured to pass through the tubular support member; and a handle coupled to the tubular support member, wherein the handle includes a tension mechanism configured to provide the tension force to the pull wire in order to place the beam in the deflected position.

In some embodiments, the system further includes a deflection catheter that includes: a catheter shaft that includes an internal lumen, a balloon affixed to the catheter shaft, and a hub affixed to the internal lumen of the catheter shaft, wherein at least a portion of the deflection mechanism is configured to be placed in the internal lumen of the catheter shaft.

In some embodiments of the system, each one of the one or more constraint members is configured to limit the displacement distance to a value such that the pull wire is prevented from forming a geometric chord of the beam when the beam is in the deflected position. In some embodiments, each one of the one or more constraint members is configured to limit the displacement distance to a value such that the pull wire forms an arc with a larger radius of curvature than that of the beam. In some embodiments, the deflection mechanism provides an expansion ratio (ER) that is in a range from about 0.15 to about 0.4.

In some embodiments of the system, the one or more constraint members includes a plurality of mini-beams including a first mini-beam operatively coupled to the beam at the distal end of the beam and a second mini-beam operatively coupled to the beam at the proximal end of the beam, wherein each one of the plurality of mini-beams is shorter than the beam. In some embodiments, the one or more constraint members includes an elastic tube that surrounds the beam and the pull wire, wherein the elastic tube is configured to stretch radially as the pull wire moves to the displacement distance away from the beam. In some embodiments, the one or more constraint members includes a plastic tube that surrounds the beam and the pull wire, wherein a cross-sectional geometry of the plastic tube includes an inner section and a curved segmented outer section, wherein the curved segmented outer section includes a plurality of segments that are separated from each other radially along the curved segmented outer section.

In some embodiments of the system, the one or more constraint members includes a plurality of rings including a first ring and a second ring, wherein each one of the plurality of rings surrounds the beam and the pull wire, wherein each one of the plurality of rings is configured to stretch radially as the pull wire moves to the displacement distance away from the beam, and wherein the first ring is located at a first axial location along the beam and the second ring is located at a second axial location along the beam.

In some embodiments of the system, the one or more constraint members include a wire mesh that surrounds the beam and the pull wire. In some embodiments, the one or more constraint members include a spring that surrounds the beam and the pull wire. In some embodiments, the one or more constraint members include a plurality of elastic members that surrounds the beam and the pull wire, wherein each respective elastic member of the plurality of elastic members includes a first wall thickness and a second wall thickness, wherein the second wall thickness of each respective elastic member is located at one or more selective axial positions of the elastic member, and wherein the second wall thickness is greater than the first wall thickness.

In some embodiments of the system, the one or more constraint members include a plurality of mini-beams including a first mini-beam operatively coupled to the beam at the distal end of the beam and a second mini-beam operatively coupled to the beam at the proximal end of the beam, wherein each one of the plurality of mini-beams is shorter than the beam, the deflection system further including a sheath configured to encapsulate the deflection mechanism in order to seal the deflection mechanism from fluid infiltration.

In some embodiments of the system, the one or more constraint members include a plurality of mini-beams including a first mini-beam operatively coupled to the beam at the distal end of the beam and a second mini-beam operatively coupled to the beam at the proximal end of the beam, wherein each one of the plurality of mini-beams is shorter than the beam, the deflection system further including a balloon catheter configured to surround the deflection mechanism.

In some embodiments of the system, the beam has a cross-sectional-width dimension and a cross-sectional-height dimension, wherein the cross-sectional-width dimension is larger than the cross-sectional-height dimension. In some such embodiments, the beam further includes a length dimension and the beam is configured to preferentially bend along the length dimension. In some embodiments, the beam has a rectangular cross section. In some embodiments, the beam has a square-shaped cross section. In some embodiments, the beam has an oval-shaped cross section. In some embodiments, the beam has a circular cross section. In some embodiments, the beam has a circular cross section that has been flattened by compression. In some embodiments, the beam includes a bi-metal strip having a first metal and a second metal, wherein the bi-metal strip is configured to bend upon application of an applied current, and wherein the applied current causes the first metal to heat at a first heat rate and the second metal to heat at a second heat rate that is different from the first heat rate. In some embodiments, the beam includes a bi-metal strip having a first metal and a second metal, wherein the bi-metal strip bends upon application of an applied current, wherein the applied current causes at least one of the first metal and the second metal to undergo a phase change.

In some embodiments, the present invention provides a deflection mechanism that includes a beam; a pull wire connected to the beam on a first end of the beam; a tubular support column connected to the beam on a second end of the beam, wherein the pull wire passes through the tubular support column; a handle connected to the support column containing a mechanism for tensioning the pull wire; and one or more constraints attached to the beam which change shape during tensioning of a pull wire to allow the pull wire to be displaced laterally from the beam during deflection but which limit the displacement do a distance less than that formed in the absence of a constraint.

In some embodiments, the present invention provides a deflection catheter that includes a balloon affixed to a catheter shaft with an internal lumen to which is affixed a hub, the internal lumen containing a deflection mechanism that includes: a beam; a pull wire connected to the beam on a first end of the beam; a tubular support column connected to the beam on a second end of the beam, wherein the pull wire passes through the tubular support column; a handle connected to the support column containing a mechanism for tensioning the pull wire; and one or more constraints attached to the beam which change shape during tensioning of a pull wire to allow the pull wire to be displaced laterally from the beam during deflection but which limit the displacement do a distance less than that formed in the absence of a constraint.

In some embodiments, the present invention provides a method for deflecting a body lumen that includes providing a deflection mechanism, wherein the deflection mechanism includes: a beam having a proximal end and a distal end, wherein the beam includes a neutral position and a deflected position, a pull wire, and one or more constraint members; the method further including coupling the pull wire to the distal end of the beam; operatively coupling the one or more constraint members to the beam; applying a tension force to the pull wire such that the beam is placed in the deflected position, wherein at least a portion of the pull wire moves to a displacement distance away from the beam during the applying of the tension force; and limiting the displacement distance of the pull wire from the beam via the one or more constraint members.

In some embodiments of the method, the limiting of the displacement distance of the pull wire includes preventing the pull wire from forming a geometric chord of the beam when the beam is in the deflected position. In some embodiments, the beam has a first radius of curvature in the deflected position, wherein the limiting of the displacement distance of the pull wire includes limiting the displacement distance to a value such that the pull wire forms an arc having a second radius of curvature, and wherein the second radius of curvature is larger than the first radius of curvature.

In some embodiments, the method further includes providing a deflection catheter that includes: a catheter shaft that includes an internal lumen, a balloon affixed to the catheter shaft, and a hub affixed to the internal lumen of the catheter shaft; the method further including placing at least a portion of the deflection mechanism in the internal lumen of the catheter shaft.

In some embodiments of the method, the one or more constraint members further include a plurality of mini-beams, wherein the plurality of mini-beams includes a first mini-beam and a second mini-beam, wherein each one of the plurality of mini-beams is shorter than the beam, the method further including: operatively coupling the first mini-beam to the beam at the distal end of the beam; and operatively coupling the second mini-beam to the beam at the proximal end of the beam.

In some embodiments of the method, the one or more constraint members further include an elastic tube, the method further including surrounding the beam and the pull wire with the elastic tube, wherein the elastic tube is configured to stretch radially as the pull wire moves to the displacement distance away from the beam.

In some embodiments of the method, the one or more constraint members include a plurality of rings including a first ring and a second ring, wherein each one of the plurality of rings is configured to stretch radially as the pull wire moves to the displacement distance away from the beam, the method further including: placing the first ring around the beam at a first axial location along the beam; and placing the second ring around the beam at a second axial location along the beam.

In some embodiments of the method, the one or more constraint members further include a plurality of mini-beams, wherein the plurality of mini-beams includes a first mini-beam and a second mini-beam, wherein each one of the plurality of mini-beams is shorter than the beam, the method further including: operatively coupling the first mini-beam to the beam at the distal end of the beam; operatively coupling the second mini-beam to the beam at the proximal end of the beam; providing a sheath; and encapsulating the deflection mechanism with the sheath in order to seal the deflection mechanism from fluid infiltration.

In some embodiments of the method, the one or more constraint members further include a plurality of mini-beams, wherein the plurality of mini-beams includes a first mini-beam and a second mini-beam, wherein each one of the plurality of mini-beams is shorter than the beam, the method further including: operatively coupling the first mini-beam to the beam at the distal end of the beam; operatively coupling the second mini-beam to the beam at the proximal end of the beam; providing a balloon catheter; and inserting the deflection mechanism into the balloon catheter.

In some embodiments, the present invention provides a system for deflecting a body lumen that includes a deflection mechanism, wherein the deflection mechanism includes: a beam having a proximal end and a distal end, wherein the beam includes a neutral position and a deflected position, and a pull wire; the system further including: means for coupling the pull wire to the distal end of the beam; and means for applying a tension force to the pull wire such that the beam is placed in the deflected position, wherein at least a portion of the pull wire moves to a displacement distance away from the beam during the applying of the tension force, and wherein the deflection mechanism further includes means for limiting the displacement distance of the pull wire from the beam.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment). Further, some embodiments include fewer than all the components described as part of any one of the embodiments described herein. Still further, it is specifically contemplated that the present invention includes embodiments having combinations and subcombinations of the various embodiments described herein and the various embodiments described by the related applications and publications incorporated by reference in paragraphs above of the present application.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first, " "second," and "third," etc., are used merely as labels, and are not intended to impose numerical requirements on their objects.

What is claimed is:

1. A deflection system for deflecting a body lumen comprising:
   a deflection mechanism, wherein the deflection mechanism includes:
   a beam having a proximal end and a distal end, wherein the beam includes a neutral position and a curved-beam deflected position, wherein the beam is configured such that, in the deflected position, the beam is curved to a curved arc having a first radius of curvature,
   a pull wire coupled to the distal end of the beam, wherein the beam is configured to be curved to the deflected position when a tension force is applied to the pull wire, and wherein at least a portion of the pull wire is configured to move to a displacement distance away from the beam when the tension force is applied to the pull wire, and
   one or more constraint members operatively coupled to the beam, wherein each one of the one or more constraint members is configured to limit the displacement distance of the pull wire from the curved beam when the tension force is applied to the pull wire, wherein the one or more constraint members include a plurality of mini-beams, wherein the plurality of mini-beams includes a first mini-beam distally coupled to the beam and a second mini-beam proximally coupled to the beam, wherein each one of the plurality of mini-beams is shorter than the beam, and wherein the pull wire is located between the beam and each respective one of the plurality of mini-beams.

2. The deflection system of claim 1, wherein the deflection mechanism further includes:
   a tubular support member coupled to the proximal end of the beam, wherein the pull wire is configured to pass through the tubular support member; and
   a handle coupled to the tubular support member, wherein the handle includes a tension mechanism configured to provide the tension force to the pull wire in order to place the beam in the deflected position.

3. The deflection system of claim 1, further comprising:
   a deflection catheter that includes:
   a catheter shaft that includes an internal lumen,
   a balloon affixed to the catheter shaft, and
   a hub affixed to the internal lumen of the catheter shaft,
   wherein at least a portion of the deflection mechanism is configured to be placed in the internal lumen of the catheter shaft.

4. The deflection system of claim 1, wherein the deflection mechanism provides an expansion ratio (ER) that is in a range from about 0.15 to about 0.4.

5. The deflection system of claim 1, wherein the one or more constraint members also include an elastic tube that surrounds the beam and the pull wire,
wherein the elastic tube is configured to stretch radially as the pull wire moves to the displacement distance away from the beam.

6. The deflection system of claim 1, wherein the one or more constraint members also include a plastic tube that surrounds the beam and the pull wire, wherein a cross-sectional geometry of the plastic tube includes an inner section and a curved segmented outer section, wherein the curved segmented outer section includes a plurality of segments that are separated from each other radially along the curved segmented outer section.

7. The deflection system of claim 1, wherein the one or more constraint members also include a plurality of rings including a first ring and a second ring, wherein each one of the plurality of rings surrounds the beam and the pull wire, wherein each one of the plurality of rings is configured to stretch radially as the pull wire moves to the displacement distance away from the beam, and wherein the first ring is located at a first axial location along the beam and the second ring is located at a second axial location along the beam.

8. The deflection system of claim 1, wherein the one or more constraint members also include a plurality of elastic members that surrounds the beam and the pull wire, wherein each respective elastic member of the plurality of elastic members includes a first wall thickness and a second wall thickness, wherein the second wall thickness of each respective elastic member is located at one or more selective axial positions of the elastic member, and wherein the second wall thickness is greater than the first wall thickness.

9. The deflection system of claim 1, further comprising:
   a sheath configured to encapsulate the deflection mechanism in order to seal the deflection mechanism from fluid infiltration.

10. The deflection system of claim 1, further comprising:
    a balloon catheter configured to surround the deflection mechanism.

11. The deflection system of claim 1, wherein the beam has a cross-sectional-width dimension and a cross-sectional-height dimension, and wherein the cross-sectional-width dimension is larger than the cross-sectional-height dimension.

12. A method for deflecting a body lumen comprising:
    providing a deflection mechanism, wherein the deflection mechanism includes:
    a beam having a proximal end and a distal end, wherein the beam includes a neutral position and a deflected position, wherein the beam includes a first radius of curvature in the deflected position,
    a pull wire, and
    one or more constraint members, wherein the one or more constraint members include a plurality of mini-beams, wherein the plurality of mini-beams includes a first mini-beam and a second mini-beam, wherein each one of the plurality of mini-beams is shorter than the beam;
    operatively coupling the first mini-beam to the beam distally;
    operatively coupling the second mini-beam to the beam proximally;
    locating the pull wire between the beam and the plurality of mini-beams;
    coupling the pull wire to the
    distal end of the beam; applying a tension,
    force to the pull wire such that the beam is placed in the deflected position, wherein at least a portion of the pull wire moves to a displacement distance away from the beam during the applying of the tension force; and
    limiting the displacement distance of the pull wire from the beam via the one or more constraint members.

13. The method of claim 12, wherein the limiting of the displacement distance of the pull wire includes preventing the pull wire from forming a geometric chord of the beam when the beam is in the deflected position.

14. The method of claim 12, wherein the limiting of the displacement distance of the pull wire includes limiting the displacement distance to a value such that the pull wire forms an arc having a second radius of curvature, and wherein the second radius of curvature is larger than the first radius of curvature.

15. The method of claim 12, wherein the one or more constraint members further include an elastic tube, the method further comprising:

surrounding the beam and the pull wire with the elastic tube, wherein the elastic tube is configured to stretch radially as the pull wire moves to the displacement distance away from the beam.

16. The method of claim 12, wherein the one or more constraint members include a plurality of rings including a first ring and a second ring, wherein each one of the plurality of rings is configured to stretch radially as the pull wire moves to the displacement distance away from the beam, the method further comprising:

placing the first ring around the beam at a first axial location along the beam; and placing the second ring around the beam at a second axial location along the beam.

17. The method of claim 12, further comprising:

providing a sheath; and encapsulating the deflection mechanism with the sheath in order to seal the deflection mechanism from fluid infiltration.

18. A system for deflecting a body lumen comprising:

a deflection mechanism, wherein the deflection mechanism includes:

a beam having a proximal end and a distal end, wherein the beam includes a neutral position and a curved-beam deflected position, and wherein the beam includes a first radius of curvature in the curved-beam deflected position, and a pull wire;

means for coupling the pull wire to the distal end of the beam; and means for applying a tension force to the pull wire such that the beam is placed in the deflected position, wherein at least a portion of the pull wire moves to a displacement distance away from the beam during the applying of the tension force, and wherein the deflection mechanism further includes:

means for limiting the displacement distance of the pull wire from the beam wherein the means for limiting the displacement distance of the pull wire includes a plurality of mini-beams, wherein the plurality of mini-beams includes a first mini-beam operatively coupled to the beam at the distal end of the beam and a second mini-beam operatively coupled to the beam at the proximal end of the beam, wherein each one of the plurality of mini-beams is shorter than the beam, and wherein the pull wire is located between the beam and the plurality of mini-beams.

* * * * *